United States Patent [19]
Hatanaka et al.

[11] Patent Number: 6,066,484
[45] Date of Patent: May 23, 2000

[54] PURINE NUCLEOSIDASE

[75] Inventors: Haruyo Hatanaka, Kyoto; Toshihiko Ashikari, Takatsuki; Jun Ogawa; Sakayu Shimizu, both of Kyoto, all of Japan

[73] Assignee: Suntory Limited, Osaka, Japan

[21] Appl. No.: 08/912,560

[22] Filed: Aug. 18, 1997

[30] Foreign Application Priority Data

Aug. 16, 1996 [JP] Japan .................................. 8-216421

[51] Int. Cl.$^7$ ............................... C12N 9/16; C12C 1/00
[52] U.S. Cl. ............................................. 435/196; 435/93
[58] Field of Search ....................................... 435/196, 93

[56] References Cited

U.S. PATENT DOCUMENTS 5,200,313 4/1993 Carrico ........................................ 435/6

FOREIGN PATENT DOCUMENTS 753 572 1/1997 European Pat. Off. .

OTHER PUBLICATIONS

Leung et al. Structure and regulation of the AMP nucleosidase gene (amn) from *Escherichia coli*. Biochemistry 28: 8726–8733, 1989.

Takagi et al., "Purification and Properties of a Bacterial Riboside Hydrolase" (XP–002104771, p. 77–86) from The Journal of Biological Chemistry, vol. 225, 1995.

Tofler et al., "A 13–Year Follow–Up of Social Drinkers", (XP–002104772, p. 479–481) from The Medical Journal of Australia, vol. 2, Oct. 31, 1981.

Thompson et al., "The Effect of Inositol and Nucleic Acid Bases on the Fermentation Rate of an Ale Yeast," *A.S.B.C. Proceedings*, 1973, p. 137–141.

Yoshino et al., "Inosine Nucleosidase from *Azotobacter Vinelandii*," *Archives of Microbiology*, vol. 119, 1978, p. 59–64.

Parkin et al., "Nucleoside Hydrolase from *Crithidia Fasciculata*," *The Journal of Biochemistry*, 1991, p. 20658–20665.

*Primary Examiner*—Karen Cochrane Carlson
*Assistant Examiner*—Devesh Srivastava
*Attorney, Agent, or Firm*—Burns, Doane, Swecker & Mathis, L.L.P.

[57] ABSTRACT

Novel purine nucleosidase derived from *Ochrobactrum anthropi* microorganisms, a gene system coding therefor, uses therefor and particularly its use in the production of beer.

2 Claims, 11 Drawing Sheets

—□— SODIUM ACETATE/HYDROCHLORIC ACID
—◇— SODIUM ACETATE/ACETIC ACID
—○— MONOPOTASSIUM PHOSPHATE/DIPOTASSIUM PHOSPHATE
—△— TRIS/HCl

— □ — SODIUM ACETATE/HYDROCHLORIC ACID
— ◇ — SODIUM ACETATE/ACETIC ACID
— ○ — MONOPOTASSIUM PHOSPHATE/DIPOTASSIUM PHOSPHATE
— △ — TRIS/HCl

─□─ SODIUM ACETATE/HYDROCHLORIC ACID
─◇─ SODIUM ACETATE/ACETIC ACID
─○─ MONOPOTASSIUM PHOSPHATE/DIPOTASSIUM PHOSPHATE
─△─ TRIS/HCl

PURINE NUCLEOSIDASE

BACKGROUND OF INVENTION

1. Field of Invention

The present invention relates to a purine nucleosidase obtained from *Ochrobactrum anthropi* and to its derivatives, and it further relates to DNA coding for the enzyme or its derivatives, to an expression vector including the DNA, to recombinant host cells transformed with the expression vector, to a process for producing a protein with purine nucleosidase activity using the recombinant host cells, to a process for producing a protein with purine nucleosidase activity using a microorganism belonging to the genus Ochrobactrum capable of producing the protein, and to a process for producing beer or wort using the protein.

2. Related Art

With the westernization and overnutrition of the diet in recent years there has been observed an increase in blood uric acid levels in adult males, leading to fears of a rising number of gout cases due to asymptomatic hyperuricemia. Free purine bases, purine nucleosides, purine nucleotides and high molecular nucleic acids in the diet are digested and absorbed in the digestive tract and decomposed to uric acid by the uric acid cycle in the liver. The vast majority of etiological observations support the view of intake of purine-rich foods as the cause of hyperuricemia and gout, and therefore reduction of ingested purines is the most important means of preventing hyperuricemia and gout.

Purine-rich foods include meat, milt, fish eggs and liver, but alcoholic beverages and especially beer also have rather high purine contents. Actual comparisons of purine contents in various alcoholic beverages by Kaneko (Kiyoko Kaneko, Japan Clin., Vol.49, No.5, 1108–1115, 1991) shows that fermented liquors such as beer, sake and wine contain larger amounts of purines than distilled liquors such as whiskey and Japanese shochu, and that among fermented liquors beer has an especially high purine content. Although the purine content of beer is only 1/100 to 1/10 that of meat, eggs or liver, the comparatively large amount of consumption thereof implies a considerable attack risk for hyperuricemia and gout.

Tofler and Woodings (O. B. Tofler and T. L. Woodings, Med. J. Aust., Vol.2, 479–481, 1981) carried out a follow-up study over 13 years using groups among a survey population classified based on amount of beer consumption, and pointed out a positive correlation between beer consumption and gout frequency. Based on such etiological research conducted to date, beer is considered to be the alcoholic beverage with the highest attack risk for hyperuricemia and gout. However, no technology has been developed for reducing purine levels of foods, including beer.

SUMMARY OF INVENTION

Included in the term "purine compounds" are free purine bases, purine nucleosides, purine nucleotides and high molecular nucleic acids. Investigation of the nature of purine compounds in the beer production process reveals absolutely no purine nucleotides or high molecular nucleic acids in wort, but a large amount of free purine bases and purine nucleosides. The free purine bases are absorbed and metabolized by yeast during fermentation and thus virtually disappear. On the other hand, purine nucleosides which make up the greater part of the purine compounds in wort are not reduced during fermentation, and they even increase when the temperature falls to 0° C. during storage after fermentation has been completed. These analysis results suggest that if the purine nucleosides in wort can be decomposed to ribose and free purine bases, the free purine bases will then be absorbed and metabolized by the yeast to realize a reduction in the amount of purine compounds in beer.

Furthermore, although microorganisms used for fermented products other than beer cannot assimilate purine nucleosides, if they are capable of utilizing free purine bases as a nutrition source it will be possible to reduce the amount of purine compounds in the fermented product in the same manner by decomposing the purine nucleosides in the raw fermentation substance to ribose and free purine bases. It has also been reported that fermentation during beer brewing is delayed if the wort has a low adenine content (Thompson, C. C., Leedham, P. A., and Lawrence, D. R., Am. Soc. Brew. Chem., Proc. 1973, p.137–141), and thus a positive effect on yeast growth is expected by decomposing the purine nucleosides to ribose and free purine bases which increases the amount of nucleic acid compounds which can be assimilated by the yeast. The same effect is also expected for fermented foods prepared with microorganisms which cannot assimilate purine nucleosides but can utilize the free purine bases as a nutrition source.

Two enzymes which are known to decompose purine nucleosides to ribose and free purine bases are purine nucleosidase and purine nucleoside phosphorylase. Of the two, purine nucleoside phosphorylase is less efficient at completely decomposing purine nucleosides in reaction solutions to ribose and free purine bases because it catalyzes both decomposition and synthesis reactions, or catalyzes cross reaction. Purine nucleosidase produces an equilibrium shifted toward the decomposition side and can therefore accomplish thorough decomposition to ribose and free purine bases, but it varies in its substrate specificity, optimum pH, optimum temperature, etc.

In the mashing step for production of wort from malt in the beer production process, decomposition of extracted purine nucleosides requires a purine nucleosidase which can utilize adenosine, inosine and guanosine as substrates under conditions of pH 5.0 to 5.5 and 50 to 80° C. As known nucleosidases with heat resistance there may be mentioned that of *Aspergillus niger*, that of *Bacillus cereus* and that of *Crithidia fasciculata*. However, *Aspergillus niger* nucleosidase has a slightly low optimum pH of 4.0 to 4.5, and cannot decompose xanthosine. Xanthosine is virtually absent in the case of beer, but for applications to other fermented foods activity against xanthosine may be required. The optimum pH and substrate specificity of *Bacillus cereus* nucleosidase has not been investigated in detail.

Based on studies by the present inventors using cell extracts, the activity against guanosine is low. *Crithidia fasciculata* nucleosidase has a high optimum pH of 8.5. Wort also contains various low molecular substances, sugars and proteins, and it has not yet been investigated whether known nucleosidases can actually act on them. Therefore, we screened natural sources for microorganism-derived purine nucleosidases which can utilize adenosine, inosine and guanosine as substrates under conditions of pH 5.0 to 5.5, 50 to 80° C. As a result, high purine nucleosidase activity was found in crushed cell solutions of *Ochrobactrum anthropi*.

Thus, the present invention provides a purine nucleosidase with the following enzymological properties:

(1) substrate specificity: acts on purine compounds;

(2) optimum pH: pH 5.0 to 7.5 for adenosine, pH 4.0 to 5.5 for guanosine and pH 5.5 for inosine as substrates;

(3) pH stability: exhibits at least 90% residual activity at pH 6.5 to 7.0 with treatment at 50° C. for 60 minutes and exhibits at least 80% residual activity at pH 6.0 to 7.0 with treatment at 30° C. for 30 minutes;

(4) optimum temperature: optimum temperature of 60° C. with adenosine or inosine substrate, optimum temperature of 50° C. with guanosine substrate;

(5) temperature stability: for adenosine as substrate, stability exhibited up to 40° C. with treatment at pH 6.0 for 30 minutes and up to 30° C. with treatment at pH 4.5 for 60 minutes;

(6) molecular weight: 172,000 (measured by gel filtration chromatography), 43,000 (subunits, measured by SDS-polyacrylamide gel electrophoresis).

The present invention further provides a purine nucleosidase having the amino acid sequence from amino acid No.1 to amino acid No.341 of SEQ NO.1, or a protein having an amino acid sequence which is that amino acid sequence modified by an addition or deletion of one or more amino acids and/or a substitution with other amino acids, and which maintains purine nucleosidase activity.

The present invention still further provides a protein encoded by DNA which can be hybridized with the full or partial nucleotide sequence represented by SEQ ID NO.1 under hybridization conditions of 40° C. to 55° C., and 6×SSC, which protein also has purine nucleosidase activity.

The present invention still further provides a gene coding for the aforementioned enzyme or protein, an expression vector including the gene, and recombinant host cells transformed with the expression vector.

The present invention still further provides a process for producing a protein with purine nucleosidase activity which is characterized by culturing the aforementioned recombinant host cells and collecting the desired enzyme protein from the culture.

The present invention still further provides a process for producing a purine nucleosidase which is characterized by culturing a microorganism belonging to *Ochrobactrum anthropi* which is capable of producing the purine nucleosidase, and collecting the desired enzyme protein from the culture.

The present invention still further provides a process for producing beer which is characterized by using nucleoside-decomposed wort obtained by allowing the aforementioned purine nucleosidase to act on wort to decompose the purine nucleosides contained in the wort to purine bases.

The present invention still further provides a process for producing wort which is characterized by allowing the aforementioned purine nucleosidase to act on wort to decompose the purine nucleosides contained in the wort to purine bases, in order to obtain nucleoside-decomposed wort.

DETAILED DESCRIPTION

Figure 1:
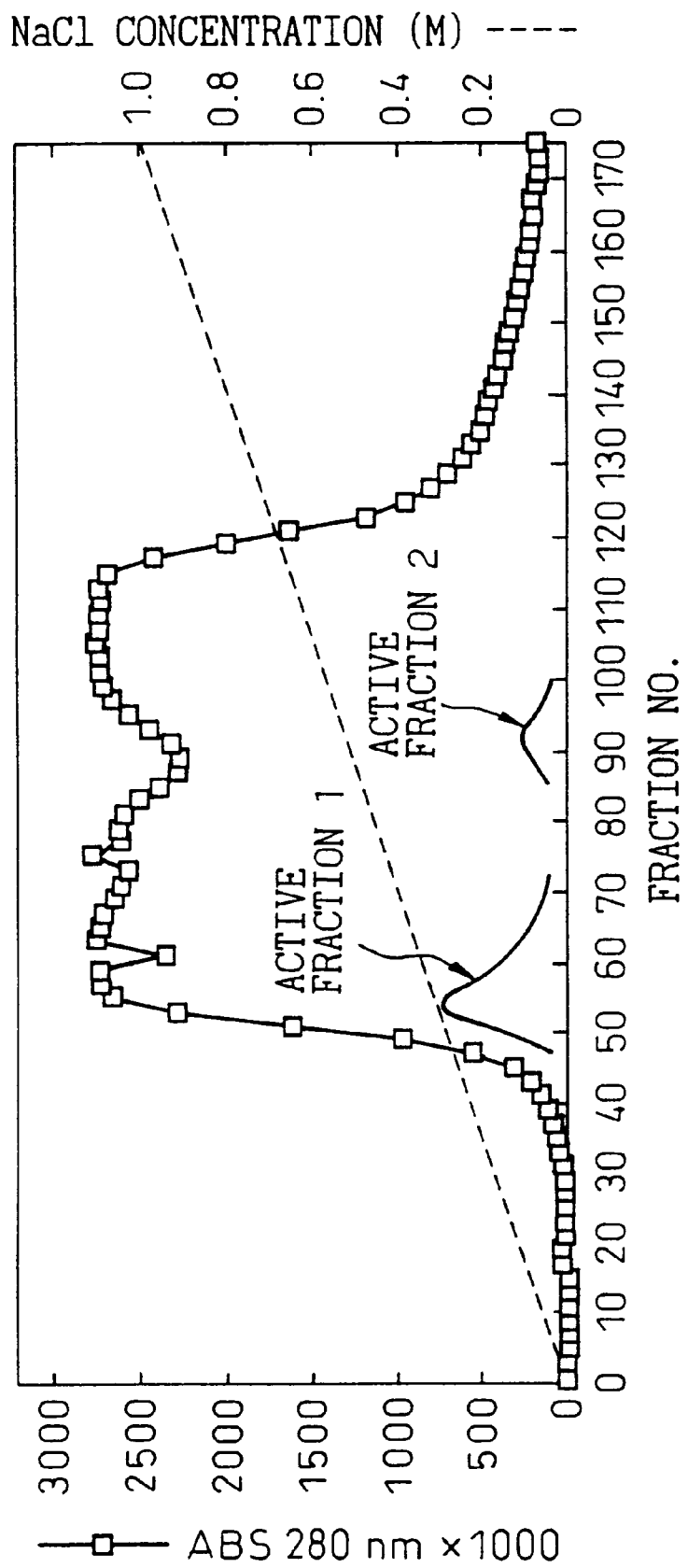
FIG. 1 shows an elution pattern for the (1st) DEAE Sephacel column chromatography.

The microorganism used to produce the enzyme purine nucleosidase of the invention or to obtain the gene coding therefor may be any one belonging to Ochrobactrum which has the ability to produce purine nucleosidase having the properties listed above, and microorganisms of the species *Ochrobactrum anthropi* may be given as an example. Representative thereof is the novel microbial strain of *Ochrobactrum anthropi* isolated by the present inventors.

This *Ochrobactrum anthropi* strain newly isolated for the present invention has the following taxonomical properties.

(a) Morphology
   (i) Cell morphology: bacillary
   (ii) Polymorphism of cells: negative
   (iii) Mobility: positive
   (iv) Sporulation: negative (b) Culturing properties
   (i) Bovillon agar plate culture (30° C., 2 days) Colony form rotund, with outward projections. Surface smooth and glossy.

(c) Physiological properties
   (i) Gram staining: negative
   (ii) Reduction of nitrate: negative
   (iii) Denitrification reaction: negative
   (iv) Indole production: negative
   (v) Acid production from glucose: negative
   (vi) Urease: positive
   (vii) Cytochrome oxidase: positive
   (viii) Catalase: positive
   (ix) Production of acid from xylose: positive
   (x) Optimum growth temperature: 28–37° C.
   (xi) Pigment production in King's B medium: negative
   (xii) O-F test (sugar: glucose): oxidation
   (xiii) Sugar assimilation
     (1) glucose +
     (2) arabinose +
     (3) mannose +
     (4) mannitol −
     (5) N-acetylglucosamine +
     (6) maltose +
     (7) gluconic acid −
     (8) capric acid +
     (9) adipic acid −
     (10) malic acid +
     (11) citric acid +
     (12) phenylacetic acid −

(d) Other properties
   (i) Esculin hydrolysis: negative
   (ii) β-galactosidase: negative
   (iii) Gelatin hydrolysis: negative
   (iv) Arginine dihydrolase: negative (v) Growth in MacConkey medium: positive
(vi) Polymyxin sensitivity: negative
(vii) Alanine utilization: positive
(viii) Glycine utilization: negative The physiochemical properties were determined using API20NE (BIO MERIEUX S.A.). A species name search was then conducted through the API20NE Analytical Profile Index based on these results; the nitrate reduction and glycine utilization differed from the description of Holmes et al. (International Journal of Systematic Bacteriology, Vol.38, No.4, 1988, p.406–416), but otherwise according to the index the strain was identified as *Ochrobactrum anthropi*. This strain was named *Ochrobactrum anthropi* SAM2125, and was internationally deposited as FERM BP-5377 at the National Institute of Bioscience and Human Technology, 1–3, Higashi 1-chome, Tsukuba-shi, Ibaraki-ken, 305 Japan on Jan. 26, 1996 in accordance with the Budapest Treaty.

The properties of the enzyme purine nucleosidase produced by the aforementioned strain SAM2125 may be summarized as follows.

(1) Substrate specificity: Acts on purine compound substrates; for example, adenosine, guanosine, inosine, xanthosine, 2'-adenosine monophosphate, 3'-adenosine monophosphate, 5'-adenosine monophosphate, 5'-guanosine monophosphate and β-nicotinamide adenine dinucleotide; does not act on pyrimidines other than 2'-CMP.

(2) optimum pH: optimum pH for adenosine, guanosine and inosine substrates: pH 5.0 to 7.5 for adenosine, pH 4.0 to 5.5 for guanosine and pH 5.5 for inosine.

(3) pH stability: exhibits at least 90% residual activity at pH 6.5 to 7.0 with treatment at 50° C. for 60 minutes and exhibits at least 80% residual activity at pH 6.0 to 7.0 with treatment at 30° C. for 30 minutes.

(4) optimum temperature: at pH 5.5, optimum temperature of 60° C. with adenosine or inosine substrate, optimum temperature of 50° C. with guanosine substrate.

(5) temperature stability: for adenosine as substrate, stability up to 40° C. with treatment at pH 6.0 for 30 minutes and up to 30° C. with treatment at pH 4.5 for 60 minutes.

(6) molecular weight: 172,000 (measured by gel filtration chromatography, TSK-G 3000 SW), 43,000 (subunit, measured by SDS-polyacrylamide gel electrophoresis).

(7) Inhibitor effects: inhibited by metal chelators, sodium selenite, 5,5'-dithiobis(2-nitrobenzoic acid), sodium cyanide, sodium fluoride and sodium azide.

(8) Metal ion effects: No metal ions found with notable activation. Inhibited by $Zn^{2+}$, $Cu^{2+}$, $Mn^{2+}$, $Hg^{2+}$ and $Ag^+$ (9) Partial amino acid sequences: Has the following amino acid sequences:
Asp-Thr-Glu-Lys-Met-Ile-Ile-Asp-Thr-Asp-Phe-Ser-Thr-Ile-Gly (N-terminus) (SEQ ID NO.2)
Glu-Phe-Asp-Lys (SEQ ID NO.3)
Thr-Ala-Phe-His-Arg-Pro-Glu-(Pro)-Thr-(Xxx)-Lys (SEQ ID NO.4)
Glu-Thr-Phe-Asp-Arg-Val-Ile-Ala-Gly-Asp-Gly-Pro-Val-Gln-Lys (SEQ ID NO.5)
Xxx-Ile-Val-Tyr-Met-Ala-Gly-Ala-Val-Asp-Val-Lys (SEQ ID NO.6)
Asp-Leu-Ile-Ala-Pro-Pro-Asp-Gly-Phe-Ala-Lys (SEQ ID NO.7)
Glu-Asp-Ala-Val-Asp-Phe-Ile-Val-Asn-Thr-Val-Lys (SEQ ID NO.8)
Val-Gly-Val-Tyr-Ala-Gly-Ala-Asn-Leu-Pro-Leu-Val-His-Asp- Pro-Arg-Ser-Phe-Glu-(Ser)-Xxx-Arg-Ala-Leu-Phe-Gly-Phe-Gly-Glu-(Ser)-Tyr-Lys (SEQ ID NO.9)
Leu-Phe-Ala-Asp-Ser-Trp-Met-Ala-Glu-Thr-Phe-Ala-Lys (SEQ ID NO.10)

The present invention further provides a purine nucleosidase having the amino acid sequence from amino acid No.1 to amino acid No.341 of SEQ ID NO.1, or a protein having an amino acid sequence modified by addition or deletion of one or more amino acids and/or a replacement of one or more amino acids with other amino acids, and which maintains purine nucleosidase activity. The number of amino acids to be modified should be such which allows modification by common gene manipulation procedures such as site-specific variable induction and the PCR.

The present invention still further provides a protein encoded by DNA which can be hybridized with the full or partial nucleotide sequence represented by SEQ ID NO.1 under hybridization conditions of 40° C. to 55° C., 6×SSC, which protein also has purine nucleosidase activity. Here, the DNA coding for the protein with purine nucleosidase activity may be used from a cDNA library or genomic DNA library obtained from, in addition to bacteria belonging to the genus Ochrobactrum, also microorganisms belonging to Serratia, Flavobacterium, Pseudomonas or Aspergillus, for example microorganisms such as *Serratia marcescens, Flavobacterium meningosepticum, Pseudomonas fluorescens* and *Aspergillus terreus*.

According to the invention, the aforementioned microorganism used for the invention is first cultured according to conventional methods to obtain a disrupted cell solution.

The purine nucleosidase alone is purified from the disrupted cell solution by chromatography with an ion-exchange column or gel filtration column, and the molecular weight, subunit structure, N-terminal amino acid sequence, partial amino acid sequences, etc. are determined. Also, synthetic DNA probes corresponding to the N-terminal amino acid sequence and partial amino acid sequences are used for screening of the *Ochrobactrum anthropi* purine nucleosidase gene to determine the entire nucleotide sequence.

It has therefore become possible to produce wort in which the purine nucleosides are decomposed to free purine bases, to produce *Ochrobactrum anthropi* purine nucleosidase in large amounts with appropriate host cells which can be easily cultured, for example prokaryotic cells such as *E. coli* or eukaryotic cells such as yeast or animal cells, and to construct means for improving the purine nucleosidase by genetic engineering methods. In other words, the present invention provides an *Ochrobactrum anthropi* protein with purine nucleosidase activity, and a gene coding therefor.

According to the present invention, proteins with purine nucleosidase activity also include those enzyme proteins with purine nucleosidase activity whose amino acid sequences have been modified. Here, a modification means that there has been a substitution, addition and/or deletion of one or more amino acid residues in the amino acid sequence of SEQ. NO.1.

Bacteria belonging to the genus Ochrobactrum may be used to obtain a protein with purine nucleosidase activity according to the invention or a gene coding therefor. For example, *Ochrobactrum anthropi* SAM 2125 (FERM BP-5377) may be used.

Some microorganisms may also exist which produce purine nucleosidases with activity which is biologically equivalent to the purine nucleosidase derived from Ochrobactrum, and the gene sequence elucidated by the present invention may be used to obtain the purine nucleosidase genes from these microorganisms as well.

The microorganism may be cultured in medium containing a suitable carbon source, nitrogen source and trace metal elements. The cultured product is then recovered, and the enzyme of interest is purified from the cell extract or culture supernatant by a combination of known methods such as precipitation, adsorption, molecular sieving and electrophoresis.

For example, the purine nucleosidase may be purified by DEAE Sephacel column chromatography, ammonium sulfate precipitation, Phenyl-Sepharose CL-4B, Sephacryl S-200HR or Mono Q HR 5/5 chromatography, etc. The N-terminal amino acid sequence or partial amino acid sequences may then be determined from the purified purine nucleosidase by a known method. Isolation of the chromosomal DNA from the microorganism, preparation of a genomic library and screening may also be carried out by known methods. Such a method is described, for example, in Sambrook et. al., Molecular Cloning, 2nd Ed. (Cold Spring Harbor, 1989).

As an illustrative explanation, the gene coding for a protein with purine nucleosidase activity according to the invention may be obtained in the following manner. Chromosomal DNA is first extracted from *Ochrobactrum anthropi* cells. It is then partially digested with a suitable restriction endonuclease such as Sau3AI and inserted into a cloning vector such as EMBL3 and used to transform host cells of *E. coli* or the like. The resulting genomic DNA library is then screened using a synthetic DNA probe corresponding to a partial amino acid sequence of the purine nucleosidase, to obtain positive clones containing DNA fragments coding for the desired protein with purine nucleosidase activity.

The DNA probe can be obtained by purifying the desired protein with purine nucleosidase activity from the Ochrobactrum culture product in the manner explained above, determining at least its partial amino acid sequence, and synthesizing the probe based on this sequence. Longer probe fragments may be prepared using the polymerase chain reaction (PCR). Alternatively, the chromosomal DNA may be completely decomposed with different restriction endonucleases and subjected to agarose gel electrophoresis, transferred to a nylon membrane or other membrane, and the aforementioned probe used to identify hybridizing DNA fragments by Southern hybridization.

The DNA fragments are then cut out from the agarose gel and collected, inserted into a cloning plasmid such as pUC, and used to transform host cells of *E. coli* or the like. The synthetic DNA probe corresponding to the partial amino acid sequence of the aforementioned purine nucleosidase may be used for screening of the clones to obtain positive clones containing the DNA fragment coding for the desired purine nucleosidase. The DNA inserted into the plasmids of the clones is then digested with a suitable restriction endonuclease to give DNA fragments which are then subcloned with a suitable vector, for example pUC18 or pUC19, and the nucleotide sequences of the inserted DNA fragment can be determined by dideoxy sequencing or the like.

Once the DNA coding for the protein with nucleosidase activity has been obtained, a person skilled in the art can easily prepare an expression vector containing the DNA and recombinant host cells transformed with the expression vector by known techniques. Specifically, expression vectors used for *E. coli* include pUC and pBR systems, pBluescript II, pTrc99A, pKK223-3, pPL-Lambda, etc. An appropriate and suitable promoter can be selected by a person skilled in the art. For example, lac promoter, tac promoter, T7 promoter, T3 promoter, trc promoter and λ PL promoter are preferred.

A GST Gene Fusion Vector (pGEX system, etc.) may be used for expression as a fused protein with Glutathione S-transferase, followed by purification with Glutathione Sepharose 4B or the like and then separation of the nucleosidase with an appropriate protease. Expression vectors to used when yeast are used as the host cells include pYE22m (Japanese Unexamined Patent Publication No. 3-97615), YRp7 (Struhl, K. et al., Proc. Natl. Acad. Sci. USA 76, 1035–1039, 1979; Stinchcomb, D. T. et al., Nature 282, 39–43, 1979), YIp5 (Struhl, K. et al., Proc. Natl. Acad. Sci. USA 76, 1035–1039, 1979) and YCp19 (Stinchcomb, D. T. et al., J. Molecule. Biol. 158, 157–179, 1982). Promoters used include GAL1 promoter, GAL7 promoter, GAL10 promoter, ADH2 promoter and GAP promoter. Appropriate and suitable host cells for expression may also be selected by a person skilled in the art from among *Bacillus subtilis*, filamentous bacteria and animal cells.

The present invention also relates to a process for producing a protein with purine nucleosidase activity, but since the culturing conditions may be appropriately selected by a person skilled in the art, no particular problems will be presented by the culturing itself so long as the aforementioned recombinant host cells can be obtained. After the transformed cells have been cultured in a culture medium containing a suitable carbon source, nitrogen source and trace metal elements and the desired enzyme protein or derivative protein has been expressed, it may be suitably collected by known methods from the culture, i.e. from the culture supernatant or from the recombinant host cells themselves after culturing. If necessary, for example, after the cells are disrupted by ultrasonic waves or a Dynamill or the like, the enzyme may be purified by a combination of known methods including precipitation, adsorption, molecular sieving and electrophoresis.

The present invention further provides a use for the protein with purine nucleosidase activity. That is, it also relates to a process for producing beer using the protein.

The present inventors have completed the present invention as a result of much research aimed at providing a production process for beer which gives lower concentrations of purine compounds, after measuring amounts of purine nucleosides, purine nucleotides, purine bases and high molecular nucleic acids in beer. "Purine bases" is a general term for derivatives of purine (9H-imidazo[4,5-d]pyrimidine) which are substituted at various sites, and includes adenine, guanine and xanthine.

"Purine nucleosides" is a general term for glucosides wherein purine bases are attached to reducing groups of sugars by N-glycoside bonds, and includes adenosine, guanosine, inosine, etc.

"Purine nucleotides" is a general term for compounds wherein the sugar portion of the purine nucleoside forms an ester with phosphoric acid, and includes adenylic acid, guanylic acid and inosinic acid.

"Purine compounds" is a general term for compounds which contain a purine skeleton of the aforementioned purine bases, purine nucleosides or purine nucleotides.

Upon measuring amounts of purine compounds in beer and during the steps of production, the present inventors have discovered the following facts:

1) The concentration of purine compounds in various commercial beer varies within 40 to 100 mg/l, but the amount of purine nucleosides present is 2 to 25 times that of purine bases. That is, the majority of purine compounds in beer exist as purine nucleosides.

2) The purine bases in wort are absorbed and metabolized by yeast during the fermentation process, virtually disappearing.

Working on these analysis results, the present inventors conducted further diligent research aimed at overcoming the problem, finally achieving the invention of a production process for beer with reduced purine compound content.

In other words, although common yeast cannot absorb purine nucleosides, they can absorb and metabolize purine bases. Thus, according to the invention, an enzyme is allowed to act on the wort to decompose the purine nucleosides in the wort to purine bases and produce nucleoside-decomposed wort, so that by using this nucleoside-decomposed wort it becomes possible to reduce the purine compound content of the beer. The nucleoside-decomposed wort has part or all of the nucleosides in the wort decomposed to purine bases by the enzyme, and the purine nucleoside content of the nucleoside-decomposed wort can be adjusted based on the amount of enzyme added, the reaction time and the reaction temperature; however, it is preferred for all of the purine nucleosides to be decomposed to purine bases, to give wort containing no purine nucleosides.

The enzyme can be employed (1) during the wort production process, (2) after wort production and before the fermentation process or (3) during the fermentation process. If the enzyme is to be employed during the wort production process, it may be added at an appropriate point at the start of wort production (saccharification) or during the wort production. If the enzyme is to be employed before the fermentation step, the enzyme is added to the wort during the wort production process, allowing it to stand for a prescribed time prior to starting fermentation, and in such a case the addition is most preferably made before boiling during the wort production process. This is because the boiling can result in inactivation of enzymes, and therefore the active enzymes in the beer product which are carried through may have some adverse effect on the quality of the beer.

If the enzyme is to be employed during the fermentation process, it is added at the start of fermentation or during fermentation. However, since the purine bases produced by the action of the enzyme must be metabolized and eliminated by the yeast, the enzyme is preferably added at the start of fermentation or during the first stage of the fermentation period.

EXAMPLES

The present invention will now be explained in more detail by way of the following examples. Unless otherwise specified, the experimental procedures were carried out according to Sambrook et al., Molecular Cloning, 2nd Edition (Cold Spring Harbor, 1989).

Example 1

Culturing of *Ochrobactrum anthropi* Purine Nucleosidase

One loopful of *Ochrobactrum anthropi* SAM2125 (FERM BP-5377) was inoculated into 5 ml of the medium described below and incubated in a test tube with shaking at 28° C. for 16 hours. It was then transferred to 50 ml of medium and incubated in 500 ml of Mayer with shaking at 28° C. for 25 hours. This was then transferred to 2 liters of medium and subjected to cultivate in a 3 liter jar with aeration and agitation at 28° C. for 47 hours. Centrifugation of the culture solution yielded 29 g of wet cells.

| Medium composition | |
|---|---|
| tryptone | 0.5% (w/v) |
| yeast extract | 0.5% |
| glucose | 0.1% |
| dipotassium phosphate | 0.1% |
| inosine | 3 mM |
| | pH 7.0 |

Example 2

Purification of *Ochrobactrum anthropi* Purine Nucleosidase

After suspending 20 g of the wet cells in 40 ml of 10 mM Tris-HCl buffer solution (pH 7.4) (hereunder referred to as "buffer"), they were disrupted in a Dynamill at 4° C. for 10 minutes. After filtering the disrupted cell suspension it was centrifuged (10,000 rpm, 60 min) and the supernatant was used as a cell-free extract. The cell-free extract (250 ml) was dialyzed for 12 hours against 5 L of buffer and then applied to a DEAE-Sephacel column (3×30 cm, 200 ml) which had been equilibrized with the buffer. The adsorbed protein was eluted with an NaCl concentration gradient from 0 to 1.0 M and the active fractions were recovered.

The purine nucleosidase activity at this time was split into two peaks (FIG. 1). Fraction nos. 46 to 69 were collected as the first active fraction and fraction nos. 85 to 101 were collected as the second active fraction. Table 1 shows the specific activities of the first and second active fractions with adenosine, inosine and guanosine as substrates. The two active fractions differ in their behavior with respect to temperature, suggesting the possibility that they are two different enzymes.

TABLE 1

| | Specific activity ($\mu$mol/min/mg) | |
|---|---|---|
| | Active fraction 1 | Active fraction 2 |
| 30° C. | | |
| adenosine | 0.70 | 0.59 |
| inosine | 1.02 | 0.63 |
| guanosine | 0.44 | 0.33 |
| 50° C. | | |
| adenosine | 3.6 | 0.45 |
| inosine | 4.3 | 0.44 |
| guanosine | 1.5 | 0.26 |

After dialyzing the active fraction (320 ml) from the (1st) DEAE-Sephacel column chromatography for 12 hours against 5 L of buffer, it was applied to a DEAE-Sephacel column (2×30 cm, 100 ml) which had been equilibrized with the buffer. The adsorbed protein was eluted with an NaCl concentration gradient from 0 to 0.35 M and the active fractions were recovered. Ammonium sulfate was added to the active fraction (16 ml) from the (2nd) DEAE-Sephacel column chromatography to 80% saturation and after thorough agitation, centrifugation was performed (10,000 rpm, 20 min) and the supernatant was obtained.

Ammonium sulfate was added to the supernatant to 100% saturation, and after thorough agitation, centrifugation was performed (10,000 rpm, 20 min) and the precipitate was recovered. The precipitate was then dissolved in 9 ml of buffer and used as the active fraction. NaCl was added to the active fraction from ammonium sulfate fractionation to a concentration of 4.0 M, and this was then supplied to a Phenyl-Sepharose CL-4B column (1×7.5 cm, 6 ml) which had been equilibrized with buffer containing 4.0 M NaCl. The adsorbed protein was eluted with an NaCl concentration gradient from 4.0 to 0 M and the active fractions were recovered. The active fraction from Phenyl-Sepharose CL-4B column chromatography (16.5 ml) was concentrated to 4 ml with an ultrafiltration membrane with a fractionating molecular weight of 30,000 and then applied to a Sephacryl S-200 HR column (1.5×80 cm, 140 ml). The protein was eluted with buffer containing 0.2 M NaCl and the active fractions were recovered.

After dialyzing the active fraction (7.5 ml) from the Sephacryl S-200 HR column chromatography for 12 hours against 5 L of buffer, it was applied to a Mono Q HR 5/5 column (0.5×5 cm, 1 ml) which had been equilibrized with the buffer. The adsorbed protein was eluted with an NaCl concentration gradient from 0 to 0.5 M and the active fractions were recovered. The obtained purified enzyme was detected as a single band by SDS-polyacrylamide gel electrophoresis. Table 2 shows a purification table with measurement using adenosine as the substrate. In the purification table, the total activity was higher after DEAE-Sephacel column chromatography than in the cell-free extract, suggesting that substances inhibiting nucleosidase activity may be present in the cell-free extract. The enzyme was confirmed to be a homotetramer with a molecular weight of 172,000 by gel filtration chromatography (TSK-G 3000SW) and subunits of 43,000 by SDS-polyacrylamide gel electrophoresis.

TABLE 2

|  | Total protein (mg) | Total activity (U) | Specific activity (U/mg) |
|---|---|---|---|
| Cell-free extract | 1980 | 616 | 0.311 |
| DEAE-Sephacel (1st) | 955 | 2600 | 2.72 |
| DEAE-Sephacel (2nd) | 105 | 2173 | 20.8 |
| Ammonium sulfate salting | 39.5 | 876 | 22.8 |
| Phenyl-Sepharose CL-4B | 20.0 | 972 | 48.5 |
| Sephacryl S-200 HR | 5.64 | 354 | 62.9 |
| Mono Q HR 5/5 | 0.183 | 53.7 | 292 |

1 U = 1 μmol/min
substrate: adenosine, reaction conditions: 50° C., pH 4.5

Example 3

Purine Nucleosidase Activity Measurement Method

The reaction solution (200 μl) contained 0.5 mM of adenosine or inosine or 0.25 mM of guanosine as the substrate, 50 mM of acetate buffer at pH 4.5 and a sufficient amount of enzyme. The reaction was initiated by addition of the enzyme, and the reaction was conducted at 50° C. for 5 minutes. The reaction was terminated by addition of 20 μl of 15% perchloric acid, and after centrifugation (35,000 rpm, 10 min) the supernatant was analyzed qualitatively by thin-layer chromatography (TLC) and quantitatively by high-performance liquid chromatography. The analysis methods were as follows.

(1) Thin-layer chromatography
Plate: Kieselgel 60F254 (Merk)
Developing solution: n-butanol/isopropanol/$H_2O$/$NH_4OH$=1:7:2:0.2 (v/v/v/v) (for adenosine and guanosine substrates), n-butanol/acetic acid/$H_2O$=5:1:1 (v/v/v) (for inosine substrate)

Detection: UV 254 nm (2) High-performance liquid chromatography

Column: Cosmosil 5C18 (4.6×100 mm)

Eluent: 0.1 M sodium chlorate tetrahydrate, 0.1% (v/v) phosphoric acid

Flow rate: 1.0 ml/min

Detection: UV 260 nm

Example 4

Substrate Specificity of Purine Nucleosidase

The substrate specificity of the purine nucleosidase was determined by thin-layer chromatography (TLC). The results are shown in Table 3. The substrate of the enzyme was generally purine compounds, and it did not act on pyrimidines except for 2'-CMP.

TABLE 3

| Substrate | Relative activity | Specific activity (μmol/min/mg) | Km (mM) | Vmax (μmol/min/mg) |
|---|---|---|---|---|
| adenosine | ++++ | 292 | 17.1 | 28.5 |
| guanosine | ++++ | 63.3 | 53.9 | 11.5 |
| inosine | ++++ | 177 | 29.6 | 18.8 |
| xanthosine | ++++ | n.d. | 63.8 | 68 |
| 2'-AMP | ++ | | | |
| 3'-AMP | ++ | | | |
| 5'-AMP | ++ | | | |
| 5'-GMP | + | | | |
| 2'-IMP | − | | | |
| 5'-IDP | − | | | |
| 5'-XMP | + | | | |
| 2'-deoxyadenosine | ++ | | | |
| 2'-chloroadenosine | ++++ | | | |
| uridine | − | | | |
| cytidine | − | | | |
| thymidine | − | | | |
| 5'-UMP | − | | | |
| 2'-CMP | + | | | |
| 5'-CMP | − | | | |
| 2'-deoxyuridine | − | | | |
| 5'-bromouridine | − | | | |
| pseudouridine | − | | | |
| β-NAD | + | | | |
| β-NADP | − | | | |
| β-NMN | − | | | |
| deamino NAD | − | | | |
| cordycepin | ++ | | | |

The specific activity was measured under conditions of 50° C., pH 4.5. The Km and Vmax were measured under conditions of 30° C., pH 4.5. The relative activity was expressed according to the following measurement method.

− not reacted
+ <10%
++ <31%
+++ <50%
++++ >50%
n.d. not determined

Example 5

Optimum pH of Purine Nucleosidase

Figure 2:
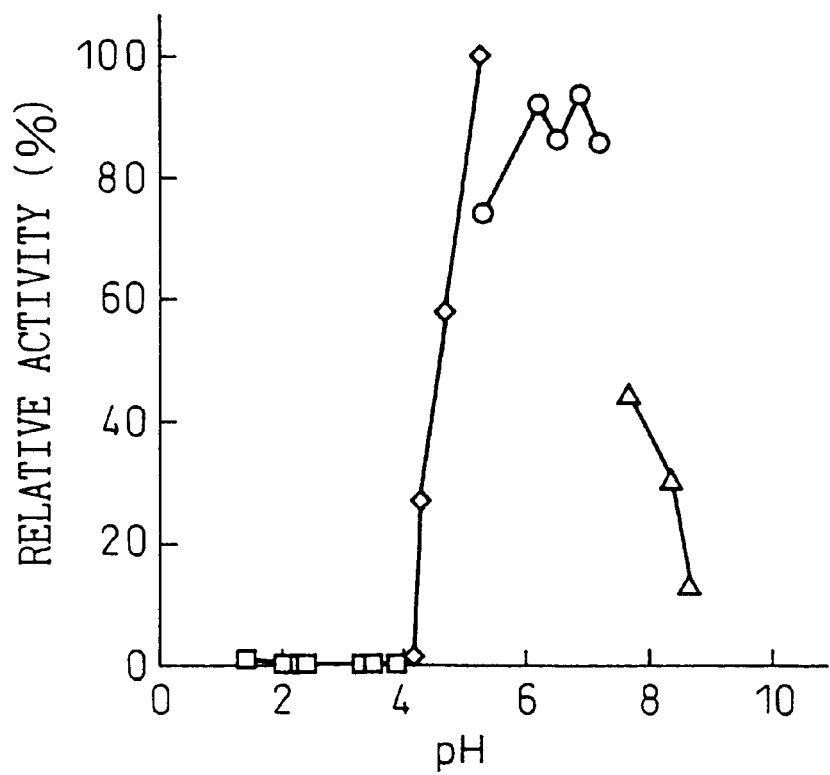
FIG. 2 shows the optimum pH for adenosine substrate.
Figure 3:
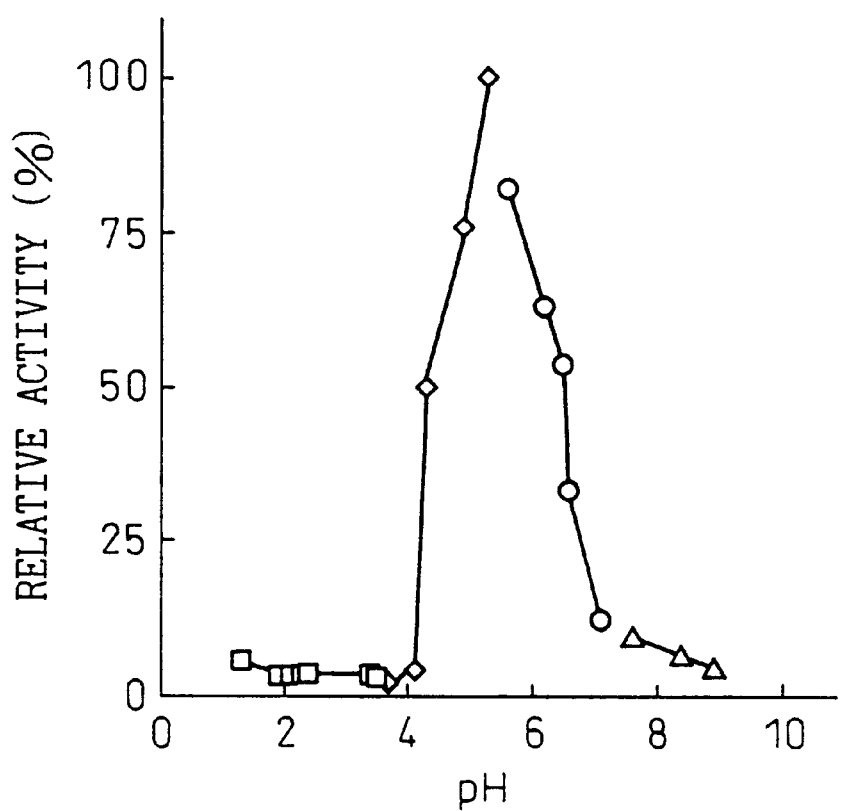
FIG. 3 shows the optimum pH for guanosine substrate.
Figure 4:
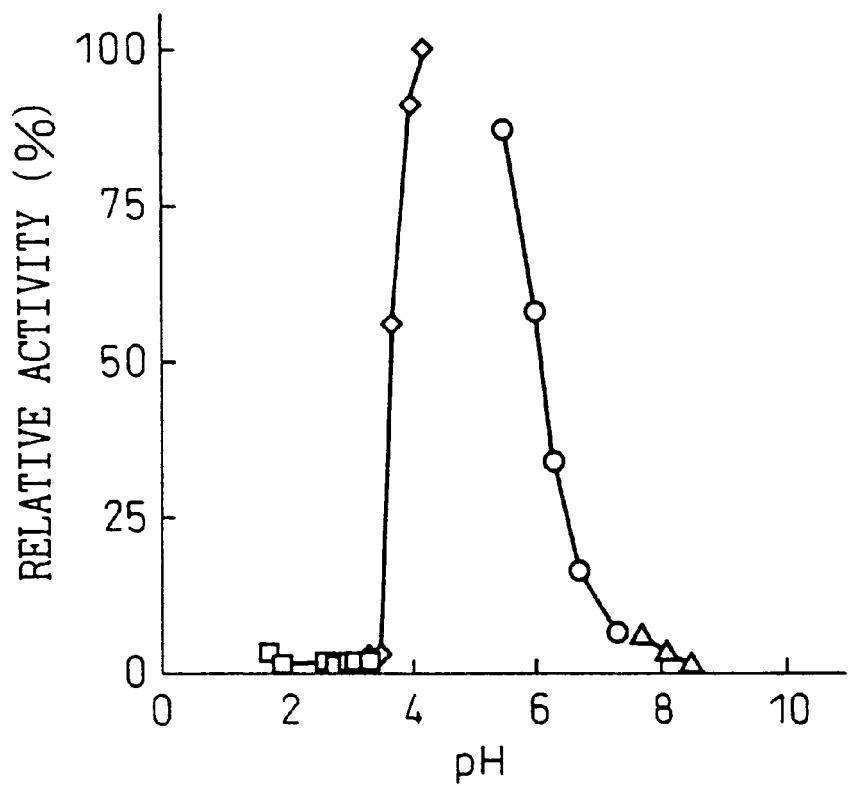
FIG. 4 shows the optimum pH for inosine substrate.

The optimum pH was determined by high-performance liquid chromatography with adenosine, guanosine and inosine substrates. The reaction solution (200 μl) contained 0.5 mM of adenosine or inosine or 0.25 mM of guanosine as the substrate, 50 mM of the buffer solutions described below and a sufficient amount of enzyme, and the reaction was conducted at 50° C. for 30 minutes. The results are shown in FIGS. 2, 3 and 4.

Buffer solutions
pH 1.0 to 4.0: sodium acetate/hydrochloric acid
pH 4.0 to 5.5: sodium acetate/acetic acid pH 5.5 to 7.5: monopotassium phosphate/dipotassium phosphate
pH 7.5 to 8.5: Tris/HCl The optimum pH was pH 5.0 to 7.5 for adenosine, pH 4.0 to 5.5 for guanosine and pH 5.5 for inosine.

Example 6

Optimum Temperature of Purine Nucleosidase

Figure 5:
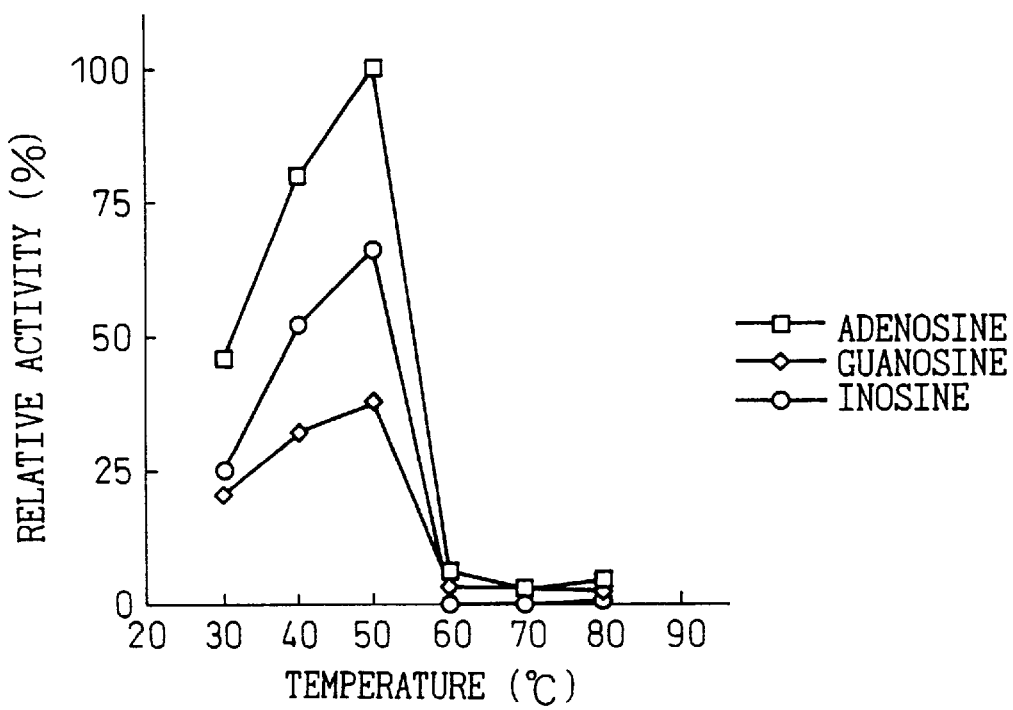
FIG. 5 shows the optimum temperature at pH 4.5.
Figure 6:
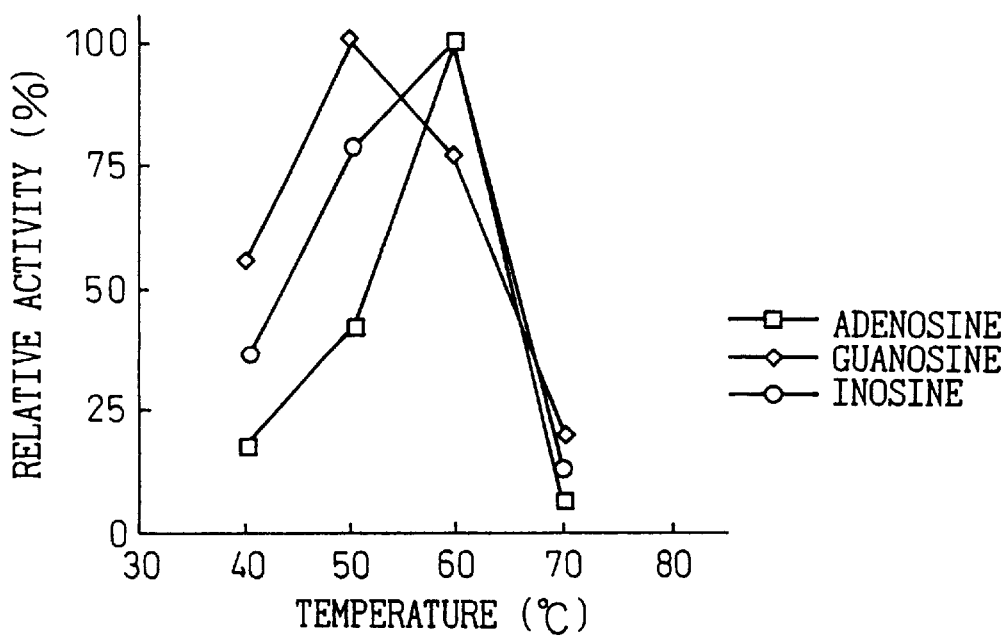
FIG. 6 shows the optimum temperature at pH 5.5.

The optimum temperature was determined by high-performance liquid chromatography with adenosine, guanosine and inosine substrates. The reaction solution (200 μl) contained 0.5 mM of adenosine or inosine or 0.25 mM of guanosine as the substrate, 50 mM of sodium acetate buffer solution (pH 4.5) or 50 mM of potassium phosphate buffer solution (pH 5.5) and a sufficient amount of enzyme, and the reaction was conducted at different temperatures for 20 minutes. The results are shown in FIGS. 5 and 6. The optimum temperature at pH 4.5 was 50° C. for adenosine, guanosine and inosine. The optimum temperature at pH 5.5 was 60° C. for adenosine and inosine and 50° C. for guanosine.

Example 7 pH Stability of Purine Nucleosidase

Figure 7:
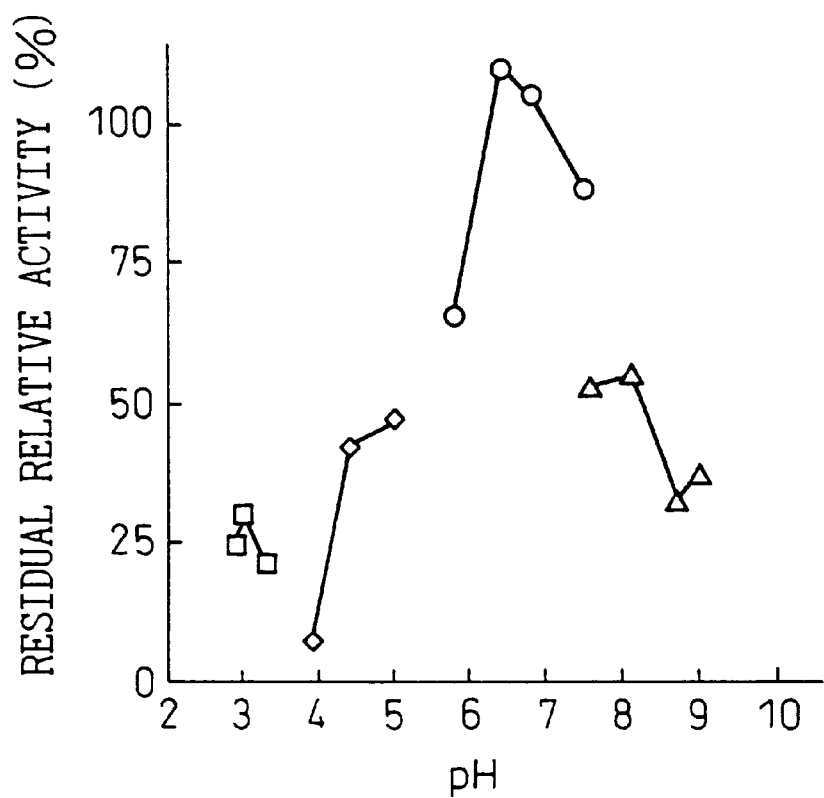
FIG. 7 shows the pH stability with heat treatment at 50° C. for 60 minutes.
Figure 8:
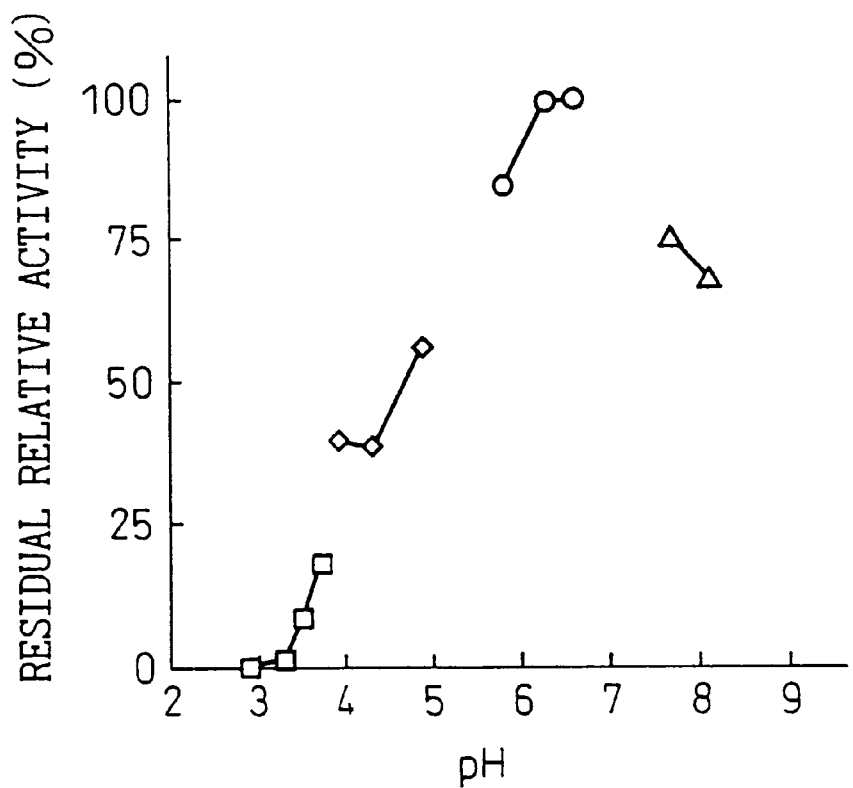
FIG. 8 shows the pH stability with heat temperature at 30° C. for 30 minutes.

The residual activity of the enzyme with inosine as the substrate was determined for treatment at 50° C. for 60 minutes and treatment at 30° C. for 30 minutes at different pH values. The buffer solutions for each pH were the same as those described above. The results are shown in FIGS. 7 and 8.

50° C., 60 minute treatment: residual activity of 90%+ at pH 6.5 to 7.0

30° C., 30 minute treatment: residual activity of 80%+ at pH 6.0 to 7.0

Example 8

Temperature Stability of Purine Nucleosidase

Figure 9:
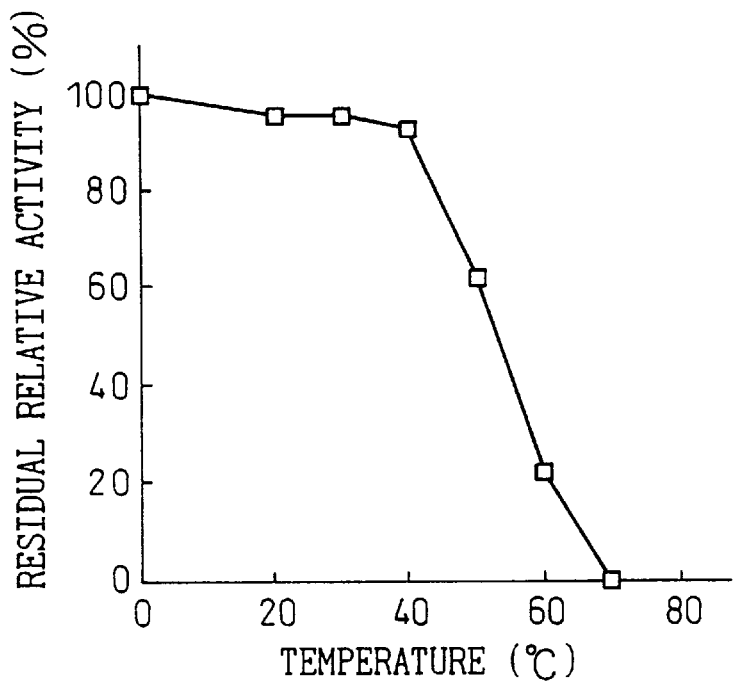
FIG. 9 shows the temperature stability with heat treatment at pH 6.0 for 30 minutes.
Figure 10:
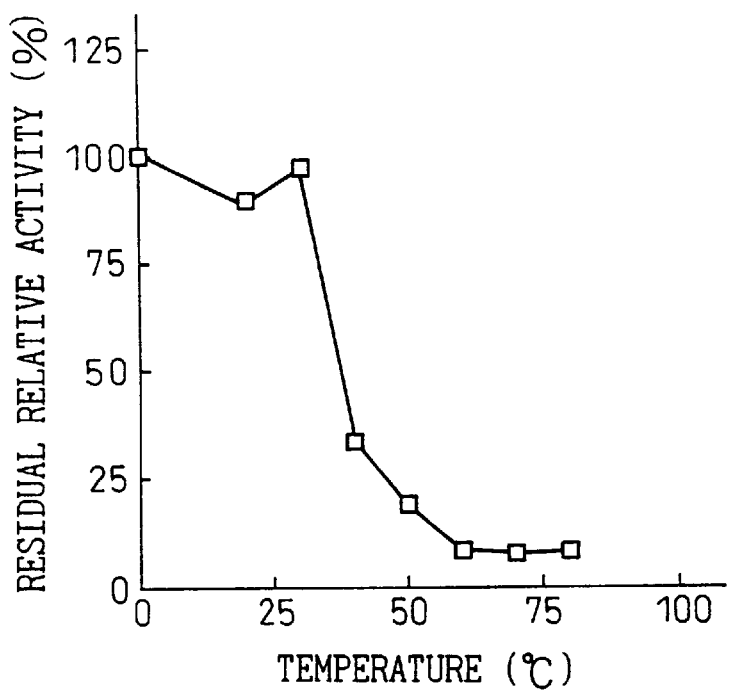
FIG. 10 shows the temperature stability with heat temperature at pH 4.5 for 60 minutes.

The residual activity of the enzyme with adenosine as the substrate was determined for treatment at pH 6.0 for 30 minutes and treatment at pH 4.5 for 60 minutes at different temperatures. The buffer solutions for each pH were the same as those described above. The results are shown in FIGS. 9 and 10.

Stable up to 40° C. with treatment at pH 6.0 for 30 minutes and up to 30° C. at pH 4.5 for 60 minutes.

Example 9

Effect of Inhibitors on Purine Nucleosidase

The activity was measured after adding 1 mM of different inhibitors to the activity measurement solution. The reaction was conducted at pH 4.5, 30° C. for 20 minutes. The results are shown in Table 4.

TABLE 4

| Inhibitor | Relative activity (%) |
|---|---|
| Not added | 100.0 |
| EDTA-Na$_2$ | 54.4 |
| 8-hydroxyquinoline | 8.5 |
| o-phenanthroline | 78.3 |
| sodium cyanide | 58.7 |
| sodium fluoride | 62.2 |
| sodium azide | 72.9 |
| NH$_2$OH·HCl | 106.6 |
| sodium arsenate | 69.4 |
| phenylhydrazine | 100.4 |
| semicarbazide | 103.4 |
| iodoacetic acid | 99.4 |
| p-CMB | 80.2 |
| N-ethylmaleimide | 107.9 |
| DTNB | 37.4 |
| N-bromosuccimide | 113.7 |

Inhibition occurred with metal chelators, sodium selenite, 5,5'-dithiobis(2-nitrobenzoic acid), sodium cyanide, sodium fluoride and sodium azide.

Example 10

Effect of Metal Ions on Purine Nucleosidase

Various metal ions were added to the activity measuring solution in an amount of 1 mM to measure the activity. The reaction was conducted at pH 4.5, 30° C. for 40 minutes. The results are shown in Table 5.

TABLE 5

| Metal | Relative activity (%) |
|---|---|
| Not added | 100.0 |
| LiCl | 103.0 |
| NaCl | 93.3 |
| KCl | 100.9 |
| RbCl | 106.5 |
| CsCl | 106.9 |
| BeSO$_4$ | 88.9 |
| MgCl$_2$ | 91.6 |
| CaCl$_2$ | 101.7 |
| BaCl$_2$ | 86.1 |
| ZnSO$_4$ | 74.9 |
| FeSO$_4$ | 92.6 |
| CuSO$_4$ | 42.7 |
| CoCl$_2$ | 82.9 |
| MnCl$_2$ | 65.5 |
| NiCl$_2$ | 91.3 |
| SnCl$_2$ | 113.2 |
| PbCl$_2$ | 111.0 |
| CdCl$_2$ | 124.9 |
| HgCl$_2$ | 39.4 |
| FeCl$_3$ | 100.0 |
| Ag$_2$SO$_4$ | 31.6 |
| AlCl$_3$ | 73.6 |

No metal ions were observed to produce any notable activation. Inhibition occurred with $Zn^{2+}$, $Cu^{2+}$, $Mn^{2+}$, $Hg^{2+}$ and $Ag^+$.

Example 11

Determination of N-terminal Amino Acid Sequence of Purine Nucleosidase

To determine the amino acid sequence from the amino terminal of the purine nucleosidase protein, the purine nucleosidase protein was purified by reducing carboxymethylation followed by reverse phase HPLC. Specifically, 108 mg of purine nucleosidase (2.5 μmole) was dissolved in 3.0 ml of modified buffer (Tris-HCl (pH 8.5) containing 6M Gdn-HCl, 10 mM EDTA-2Na) and incubated at 50° C. for one hour. After adding 143 μmole (10 μl) of 2-mercaptoethanol and performing nitrogen substitution on the reaction system, incubation was continued at 37° C. for one hour. Next, 150 μl of 1 M of sodium iodoacetate (0.207 g/ml, dissolved in modified buffer) was added, and the pH was adjusted to 8.0 to 8.5 with NaOH solution. After nitrogen substitution of the reaction system, it was blocked from light and incubated at 37° C. for one hour.

During this period the reaction system was kept at pH 8.0 to 8.5. After the reaction, the reaction solution was adequately dialyzed against $H_2O$. The dialysate solution was subjected to reverse phase HPLC under the conditions described below, and the protein fractions were collected, concentrated and freeze-dried (reverse phase HPLC conditions—column: Zolbax Pro10 PROTEIN PLUS20ϕ; flow rate: 4.0 ml/min; mobile phase: A=0.05% TFA in $H_2O$, B=$CH_3CN$:A=8:2 (v/v); detection: A280). The protein yield was 16%. A protein with a molecular weight of approximately 4 K was confirmed in the protein fractions by SDS-PAGE. The N-terminal amino acid sequence of the 5 nmol of reducing carboxymethylated purine nucleosidase protein prepared earlier was analyzed with a gas-phase protein sequencer (product of Shimazu Laboratories) and confirmed to be the following sequence.

Asp-Thr-Glu-Lys-Met-Ile-Ile-Asp-Thr-Asp-Phe-Ser-Thr-Ile-Gly (SEQ. NO.2)

Example 12

Determination of Partial Amino Acid Sequences of Purine Nucleosidase

A 48 nmole (2.0 mg) portion of reducing carboxymethylated purine nucleosidase was suspended in 100 μl of 0.01 M Tris/HCl buffer solution at pH 9.0. After adding 2 μl of a 1% solution of lysyl endopeptidase (0.1 M Tris/HCl buffer at pH 9.0) the solution was incubated at 35° C. for 6 hours. The cloudy matter in the solution disappeared immediately upon addition of the enzyme, giving a clear solution. After the reaction the solution was frozen. The reaction was terminated by drying. After the freeze-drying, the residue was dissolved in 70% formic acid and used for HPLC.

The resulting lysyl endopeptidase digestion product was subjected to reverse phase HPLC to separate the peptide fragments (reverse phase HPLC conditions—column: Bakerbold Widepore C4 (350 Angstroms) 6ϕ×250; flow rate: 1.0 ml/min; pressure: 80 kg/cm²; temperature: ambient; mobile phase: A=0.05% TFA in $H_2O$, B=$CH_3CN$:A=8:2 (v/v); detection: A220). Each of the resulting peaks were further purified by reverse phase HPLC. The amino acid sequences of the purified peptides were then determined. Among them, the following 8 peptide sequences were determined with a gas-phase protein sequencer (product of Shimazu Laboratories).

Peptide 1: Glu-Phe-Asp-Lys (SEQ. NO.3)
Peptide 2: Thr-Ala-Phe-His-Arg-Pro-Glu-(Pro)-Thr-(Xxx)-Lys (SEQ. NO.4)
Peptide 3: Glu-Thr-Phe-Asp-Arg-Val-Ile-Ala-Gly-Asp-Gly-Pro-Val-Gln-Lys (SEQ. NO.5)
Peptide 4: Xxx-Ile-Val-Tyr-Met-Ala-Gly-Ala-Val-Asp-Val-Lys (SEQ. NO.6)
Peptide 5: Asp-Leu-Ile-Ala-Pro-Pro-Asp-Gly-Phe-Ala-Lys (SEQ. NO.7)
Peptide 6: Glu-Asp-Ala-Val-Asp-Phe-Ile-Val-Asn-Thr-Val-Lys (SEQ. NO.8)
Peptide 7: Val-Gly-Val-Tyr-Ala-Gly-Ala-Asn-Leu-Pro-Leu-Val-His-Asp-Pro-Arg-Ser-Phe-Glu-(Ser)-Xxx-Arg-Ala-Leu- Phe-Gly-Phe-Gly-Glu-(Ser)-Tyr-Lys (SEQ. NO.9)
Peptide 8: Leu-Phe-Ala-Asp-Ser-Trp-Met-Ala-Glu-Thr-Phe-Ala-Lys (SEQ. NO.10)

* residues in parentheses are unconfirmed
* Xxx signifies an undecodable residue Example 13

Cloning of *Ochrobactrum Anthropi* Purine Nucleosidase Gene

Unless otherwise specified, the experiment described below was carried out according to Sambrook et al., Molecular Cloning, 2nd Edition (Cold Spring Harbor, 1989).

(1) Acquisition of Genomic DNA

The genomic DNA was prepared according to Methods in Molecular Biology, Vol.2 (Humana Press, Inc. 1984). That is, about 10 g of *Ochrobactrum anthropi* cells were suspended in 20 ml of TES buffer (10 mM Tris-HCl (pH 8.0); 10 mM NaCl; 1 mM EDTA).

After adding 200 mg of SDS, 1 ml of 2% lysozyme solution and 1 ml of 0.5 M EDTA, the mixture was gently stirred at room temperature until lysis of the cells. An equivalent of phenol/chloroform was added prior to thorough gentle mixing. Centrifugation was performed at 20,000 g for 15 minutes at room temperature and the top layer was recovered. This procedure was repeated 3 times, until the protein between the upper and lower layers virtually disappeared. A 1/10 volume of 3 M sodium acetate solution was added and mixed with the recovered aqueous layer, and then a 2-fold volume of ethanol was slowly added thereover and the DNA appearing at the interface was rolled up on a glass rod.

The DNA was dissolved in 15 ml of TES buffer, and RNase was added to 50 μg/ml prior to incubation at 37° C. for one hour. Proteinase K was then added to 50 μg/ml prior to further incubation at 37° C. for one hour. An equivalent of phenol was added, and extraction and ethanol precipitation were carried out in the same manner as described above. The recovered DNA was rinsed with 70% ethanol and then with ethanol, after which it was dried with a vacuum desiccator and dissolved in TE buffer (10 mM Tris-HCl (pH 8.0); 0.1 mM EDTA) to obtain the DNA.

(2) Southern Hybridization of Genomic DNA

The obtained genomic DNA was digested with restriction endonucleases such as EcoRI, EcoRV, HindIII, PstI, HincII and XbaI and subjected to electrophoresis with 0.8% agarose gel. The agarose gel was treated with 0.25 N hydrochloric acid for 20 minutes and then 1.5 M NaCl, 0.5 M NaOH for 30 minutes, after which the DNA was transferred from the agarose gel to a nylon membrane (Amersham). The transfer was carried out according to the method of Reed and Mann (Nucleic Acids Research, Vol.3, 7207–7221, 1985). After air drying the membrane, DNA-DNA hybridization was performed according to the method of Jeffrey and Flavell (Cell 12: 439—439, 1977).

Specifically, the DNA-immobilizing membrane filter was immersed for 30 minutes in a hybridization solution at 65° C. (6×SSC, 5×Denhardt's solution, 0.5% SDS, 10 μg/ml salmon sperm DNA). The membrane was transferred to a thick nylon bag and 106–108 cpm/μg of 32P-labelled probe DNA was added for reaction in the hybridization solution at 48° C. for 16–20 hours. After removing the hybridization solution, the membrane filter was washed 4 times in a washing buffer solution [2×SSC, 0.1% SDS (W/V)] at 48° C. for 15 minutes.

After drying the membrane filter, an X-ray film and intensifying screen were used for autoradiography at −80° C. The probe DNA used was the synthetic DNA 5'-GAPyACIGAPuAAPuATGATIATIGAPyACIGAPyTT-3' (Py representing thymine or cytosine, Pu representing adenine or guanine), a nucleotide sequence corresponding to the N-terminal amino acid sequence. As a result, positive bands with different lengths were detected for the DNA digested with each restriction endonuclease. In addition to the strongly hybridized bands, weakly hybridized bands were also confirmed.

(3) Screening with Synthetic DNA

DNA digested with restriction endonucleases such as EcoRI, EcoRV, HindIII, PstI, HincII and XbaI was subjected to electrophoresis with 0.8% agarose gel, and the DNA fragments with lengths corresponding to the bands detected by the Southern hybridization were recovered and extracted from the agarose gel. Each of the fragments were then ligated with pUC19 which had been digested with appropriate restriction endonucleases and were used to transform *E. coli* JM109. The colonies were transferred to plates at 4° C. when their diameters reached 1–2 mm after culturing at 37° C. A nylon membrane (product of Amersham) was placed over each plate, holes were opened at a few locations using an injection needle, and the mutual positions of the plate and membrane were fixed. The membrane was later removed and allowed to stand for 15 minutes on filter paper which had been immersed in a modified solution (1.5 M NaCl, 0.5 M NaOH) with the plaque side facing upward.

The membrane was then placed and allowed to stand for 15 minutes on filter paper containing a neutralizing solution (1.5 M NaCl, 0.5 M Tris-HCl (pH 7.2), 1 mM EDTA). After an additional 15 minutes on filter paper containing the neutralizing solution, the membrane was dried. The DNA was fixed by 2–5 minutes of irradiation on a UV transilluminator with the colony side facing upward. The membrane was then washed with 2×SSC to remove the cellular residue. The DNA-DNA hybridization was conducted exactly according to the method of Jeffrey and Flavell (Cell 12: 439–439, 1977).

After removing the hybridization solution, the membrane filter was washed 4 times in a washing buffer solution [2×SSC, 0.1% SDS (W/V)] at 48° C. for 15 minutes. After drying the membrane filter, an X-ray film and intensifying screen were used for autoradiography at −80° C. As a result, various positive clones were obtained from those having EcoRI fragments introduced and from those having HindIII fragments introduced.

Plasmid DNA was prepared from these positive clones (EcoRI fragments: E1, E2, E3; HindIII fragments: H1, H2, H3) and upon digestion with restriction endonucleases including EcoRI, HindIII and EcoRV and electrophoresis on 0.8% agarose gel, E1, E2, E3 and H1, H2, H3 exhibited the same respective restriction enzyme patterns. Also, upon transfer of the DNA from the agarose gel to a nylon membrane and Southern hybridization, E1, E2, E3 and H1, H2, H3 hybridized to the same respective fragments.

(4) Sequencing

Plasmid DNA prepared from a positive clone (H1) was cut with various restriction endonucleases and subjected to agarose gel electrophoresis, and a restriction enzyme map of the inserted fragments was constructed. Each of the DNA fragments was recovered and extracted from the agarose gel and subcloned in pUC19. Upon sequencing with a DNA sequencer (Perkin-Elmer Applied), the nucleotide sequences corresponding to the N-terminal amino acid sequence and partial amino acid sequences were found.

(5) Comparison of Nucleotide Sequences and Amino Acid Sequences

The nucleosidase-coding region of the nucleotide sequence for nucleosidase chromosomal DNA consists of the amino acid sequence of 363 residues in the Sequence List beginning from the initiation codon ATG and ending at the termination codon TGA. The amino acid sequence from the amino terminal of nucleosidase which was elucidated in Example 11 is an amino acid sequence of a total of 15 residues beginning from the residue No.1 Asp in the Sequence List to the following residue No.15 Gly, and it matched completely with the amino acid sequence deduced from the DNA sequence.

Confirmation was also made of the nucleotide sequences corresponding to the other determined partial amino acid sequences (peptide 1: from the 317th residue Gln to the 320th residue Lys; peptide 2: from the 99th residue Thr to the 109th residue Lys; peptide 3: from the 226th residue Glu to the 240th residue Lys; peptide 4: from the 171st residue Xxx to the 182nd residue Lys; peptide 5: from the 110th residue Asp to the 120th residue Lys; peptide 6: from the 127th residue Glu to the 138th residue Lys; peptide 7: from the 67th residue Val to the 98th residue Lys; peptide 8: from the 241st residue Leu to the 253rd residue Lys).

From these results it was determined that the cloned chromosomal DNA was the nucleosidase gene. The peptide portion from Met encoded by the initiation codon ATG to the 22nd residue which was determined from the nucleotide sequence is a sequence not present in the mature nucleosidase, and thus it was believed that this portion is either the signal peptide or the pro sequence.

Example 14

Cloning of Other Purine Nucleosidases

When the acquired full length purine nucleosidase gene was used as a probe for Southern hybridization with genomic DNA of *Ochrobactrum anthropi*, weakly hybridizing fragments were also found other than the purine nucleosidase gene, as mentioned in Example 13 (2). Other purine nucleosidases can be cloned from these fragments using the same methods described in Example 13(3).

Also, purine nucleosidase genes from organisms other than *Ochrobactrum anthropi* can also be cloned by the same method. For example, hybridized bands were also found upon hybridization (40° C.) using portions of purine nucleosidase genes obtained from *Serratia marcescens, Flavobacterium meningosepticum, Pseudomonas fluorescens* and *Aspergillus terreus* as probes.

Example 15

Production of Nucleoside-decomposed Wort

Figure 11:
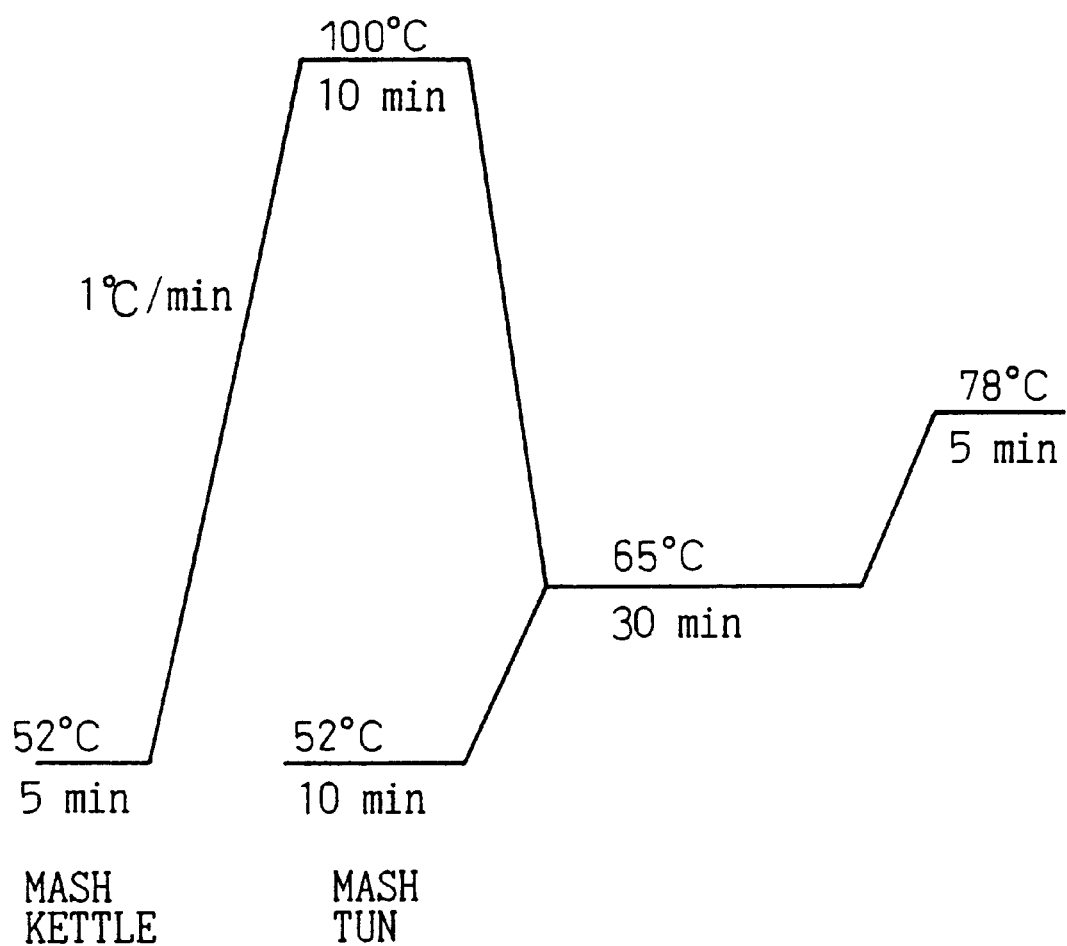
FIG. 11 shows a time-temperature curve for a mash kettle and mash tun during wort production.
Figure 12:
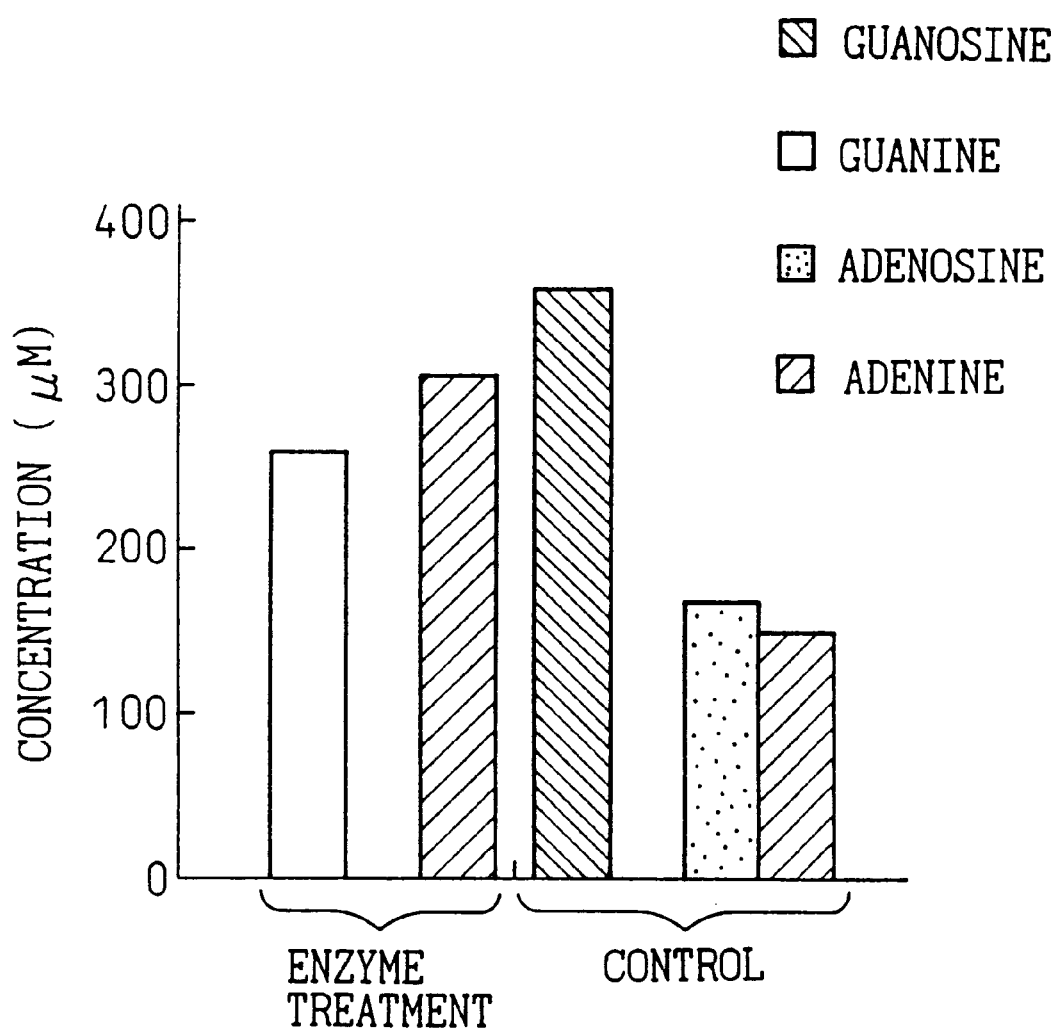
FIG. 12 is a graph showing the results of purine analysis of wort produced with addition of enzyme and wort produced without addition of enzyme.

FIG. 11 shows time-temperature curves for a mash kettle and mash tun during wort production. The proportions of starting materials in the mash kettle and mash tun are shown in Table 6. In this production process, approximately 20,000 U of *Ochrobactrum anthropi* nucleosidase which had been heat treated, salted out and partially purified by ion-exchange chromatography or gel filtration chromatography (substrate: inosine, reaction temperature: 60° C.) (1 U is the amount of enzyme which decomposes 1 μmol of inosine in 1 minute) was added to the mash tun with crushed malt to produce wort. FIG. 12 shows the analysis results for purines in wort produced with addition of the enzyme and wort produced without addition of the enzyme. No purine nucleosides were detected in the wort with the enzyme added, and the amount of purine bases increased. This wort will hereunder be referred to as nucleoside-decomposed wort.

TABLE 6

| Starting material | | Stock boiler | Stock tank |
|---|---|---|---|
| Malt | European | 6 kilograms | 12 kilograms |
| | U.S. or | 6 kilograms | 12 kilograms |
| | Canadian | | |
| Water | | 42 liters | 84 liters |
| Calcium chloride | | none | 43 grams |

Example 16

Beer Brewing Using Nucleoside-decomposed Wort

Figure 13:
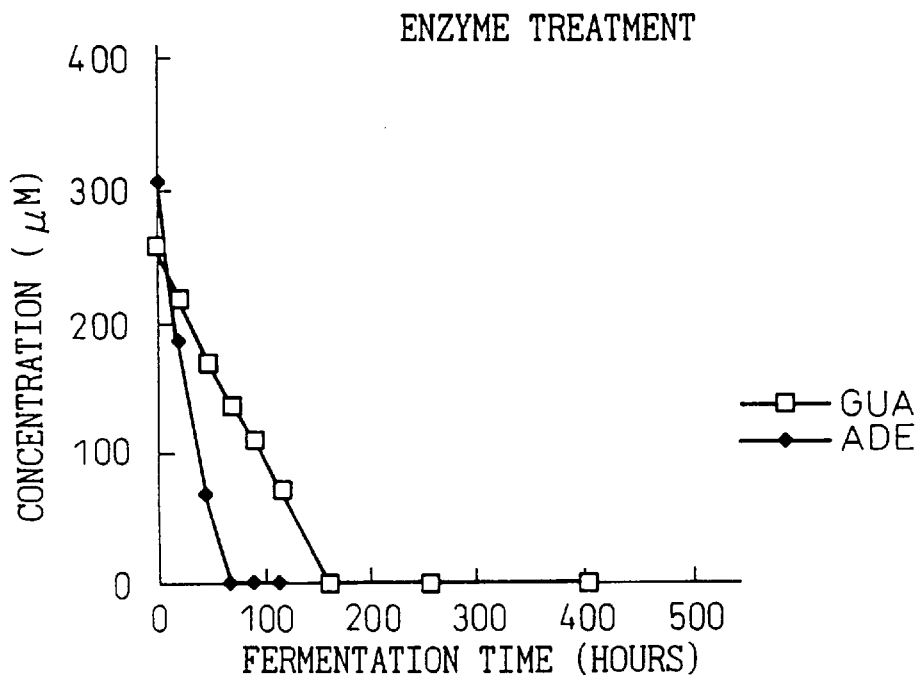
FIG. 13 shows the change in purines during fermentation using the nucleoside-decomposed wort produced in Example 16 and normal wort.
Figure 14:
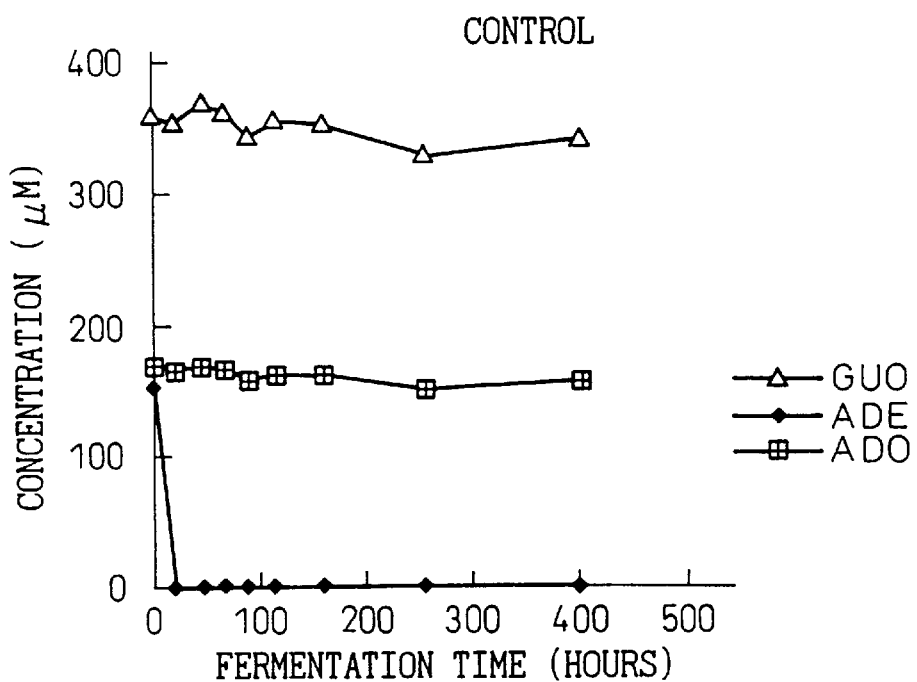
FIG. 14 shows the change in purines during fermentation using the nucleoside-decomposed wort produced in Example 16 and normal wort.

Beer was brewed using the nucleoside-decomposed wort produced in Example 15 and normal wort. Beer yeast was suspended in 2 liters of wort at a wet weight of 10.5 g and fermented at 12° C. for 8 days. It was then stored at 4° C. for 5 days. FIG. 13 shows the changes in purines during fermentation. All of the adenine was assimilated during the fermentation period. The amount of guanine in the fermentation solution decreased with time, becoming undetectable by the end of fermentation.

An amount of guanine minus about 90 μM was assimilated by the yeast. Consequently, the amount of purine corresponding to a total of 260 μM in the wort disappears during the fermentation process. Since the amount of purines in the beer brewed using the wort produced without enzyme treatment was a total of 500 μM while the amount of purines in the beer brewed using the enzyme-treated wort was a total of 180 μM, it was possible to produce beer with a total reduction of 320 μM of purines. The fermentation was roughly the same in terms of yeast growth and extract consumption, nor was there any notable difference in taste.

According to the invention *Ochrobactrum anthropi*-derived nucleosidase was purified and its features identified. This enzyme is capable of decomposing purine nucleosides such as adenosine, inosine, guanosine and xanthosine at an acidity of pH 5.5 and 60° C., and therefore the enzyme may be used to decompose purine nucleosides to purine bases during wort production. It thus becomes possible to lower the purine content of beer products. In addition, the nucleosidase gene was obtained and its nucleotide sequence and corresponding amino acid sequence were determined. According to the present invention, *Ochrobactrum anthropi* nucleosidase can be expressed in large amounts by genetic engineering techniques, and the nucleosidase can be further improved by protein engineering methods.

We claim:

1. A purified purine nucleosidase with the following enzymological properties:

(1) substrate specificity: acts on purine compounds;
   (2) optimum pH: pH 5.0 to 7.5 for adenosine, pH 4.0 to 5.5 for guanosine, and pH 5.5 for inosine as substrates;
   (3) pH stability: exhibits at least 90% residual activity at pH 6.5 to 7.0 with treatment at 50° C. for 60 minutes and exhibits at least 80% residual activity at pH 6.0 to 7.0 with treatment at 30° C. for 30 minutes;
   (4) optimum temperature: optimum temperature of 60° C. with adenosine or inosine substrate, optimum temperature of 50° C. with guanosine substrate;
   (5) temperature stability: for adenosine as substrate, stability exhibited up to 40° C. with treatment at pH 6.0 for 30 minutes and up to 30° C. with treatment at pH 4.5 for 60 minutes;
   (6) molecular weight: 172,000 (measured by gel filtration chromoatography), 43,000 (subunits, measured by SDS-polyacrylamide gel electrophoresis).

2. A purified purine nucleosidase protein having an amino acid sequence from amino acid number 1 to amino acid number 341 of SEQ ID NO:2.

* * * * *

UNITED STATES PATENT AND TRADEMARK OFFICE
CERTIFICATE OF CORRECTION

PATENT NO.    : 6,066,484
DATED         : May 23, 2000
INVENTOR(S)   : Haruyo Hatanaka et al.

It is certified that error appears in the above-identified patent and that said Letters Patent is hereby corrected as shown below:

Column 3,
Line 57, replace "guanosine" with -- inosine --.
Line 58, replace "inosine" with -- guanosine --.

Signed and Sealed this

Thirtieth Day of December, 2003

JAMES E. ROGAN
*Director of the United States Patent and Trademark Office*

SEQUENCE LISTING

```
<160> NUMBER OF SEQ ID NOS: 11

<210> SEQ ID NO 1
<211> LENGTH: 1550
<212> TYPE: DNA
<213> ORGANISM: Ochrobactrum anthropi
<220> FEATURE:
<221> NAME/KEY: CDS
<222> LOCATION: (286)..(1374)
<220> FEATURE:
<221> NAME/KEY: sig_peptide
<222> LOCATION: (286)..(349)
<220> FEATURE:
<221> NAME/KEY: mat_peptide
<222> LOCATION: (352)..(1374)

<400> SEQUENCE: 1
ttcttgtaac atgaccacca tacactcaat caaaaacaga atagaatttt cgagtcaata      60
tgaaacggtt cattgatatc aatcgtgatt tcatcaaata gcctccctat tttggcgaca     120
taactgacgc aatgacccgt ttttcctgcc atgatgaacc atttgaatgg ctggacaaga     180
ggattgtcag ttgttacgtt tccaagatga accgtttcat ttcgataatg taacattttt     240
ctgaaaatag cggttcagtc tttgggagaa gaggaggagt tttcg atg aaa cga att     297
                                                    Met Lys Arg Ile
                                                            -20 tta gcc gct gtt tgt atc gct gcg agc act tta ctc gcg cta ccg gcg       345
Leu Ala Ala Val Cys Ile Ala Ala Ser Thr Leu Leu Ala Leu Pro Ala
        -15                 -10                  -5 cag gcc gac act gag aaa atg atc att gat acc gat ttc agc aca att       393
Gln Ala Asp Thr Glu Lys Met Ile Ile Asp Thr Asp Phe Ser Thr Ile
    -1   1                   5                  10 ggt gat gat ggt cag gtc ttg atc atg gcc gca cag ctc tac aaa caa       441
Gly Asp Asp Gly Gln Val Leu Ile Met Ala Ala Gln Leu Tyr Lys Gln
 15                  20                  25                  30
```

```
ggc gca att gat ctc ctt ggc gtc act gtt gtc act ggc aat aac tgg      489
Gly Ala Ile Asp Leu Leu Gly Val Thr Val Val Thr Gly Asn Asn Trp
            35                  40                  45 ctg aag cag gaa gtt gcc gat gcg ctt cgc gcc gtg gag cgt ttg ggc      537
Leu Lys Gln Glu Val Ala Asp Ala Leu Arg Ala Val Glu Arg Leu Gly
        50                  55                  60 att gag gac aaa gtt ggc gtc tat gcg gga gcc aac tta ccg ttg gtg      585
Ile Glu Asp Lys Val Gly Val Tyr Ala Gly Ala Asn Leu Pro Leu Val
            65                  70                  75 cat gat ccc cgc agc ttt gaa agc gag cga gcg ctg ttc ggt ttt ggc      633
His Asp Pro Arg Ser Phe Glu Ser Glu Arg Ala Leu Phe Gly Phe Gly
    80                  85                  90 gaa agc tac aag act gct ttt cat cgt cct gaa cca acc gaa aaa gac      681
Glu Ser Tyr Lys Thr Ala Phe His Arg Pro Glu Pro Thr Glu Lys Asp
95                  100                 105                 110 ttg att gct ccg ccc gat ggc ttt gca aag aag gca aag ctc gag aaa      729
Leu Ile Ala Pro Pro Asp Gly Phe Ala Lys Lys Ala Lys Leu Glu Lys
                115                 120                 125 gaa gac gct gtc gat ttt ata gtc aat acg gtt aag gcc aac ccg aat      777
Glu Asp Ala Val Asp Phe Ile Val Asn Thr Val Lys Ala Asn Pro Asn
            130                 135                 140 gaa gta acg ctt ctg gtt att gga cct gtc acg aat gtc gct ctc gcc      825
Glu Val Thr Leu Leu Val Ile Gly Pro Val Thr Asn Val Ala Leu Ala
                145                 150                 155 atc cgc aag agc cca gaa atc gtg ccg ctt atc aag cgt atc gtc tac      873
Ile Arg Lys Ser Pro Glu Ile Val Pro Leu Ile Lys Arg Ile Val Tyr
        160                 165                 170 atg gcg ggt gct gtc gat gtc aaa ggc aac acg aca cct gca gca gaa      921
Met Ala Gly Ala Val Asp Val Lys Gly Asn Thr Thr Pro Ala Ala Glu
175                 180                 185                 190 atg aat gtc tgg gtc gat ccg gaa gcc gca cgt atc gtc atg cgc gcg      969
Met Asn Val Trp Val Asp Pro Glu Ala Ala Arg Ile Val Met Arg Ala
                195                 200                 205 cca att gaa caa gct atg att ccg ttg gat gtg acc gat att aca caa     1017
Pro Ile Glu Gln Ala Met Ile Pro Leu Asp Val Thr Asp Ile Thr Gln
            210                 215                 220 ctt gat aaa gag acg ttt gac cgg gtg atc gcc ggt gac ggc cca gtt     1065
Leu Asp Lys Glu Thr Phe Asp Arg Val Ile Ala Gly Asp Gly Pro Val
        225                 230                 235 caa aaa ctc ttt gca gat agc tgg atg gcc gag acc ttt gca aaa gat     1113
Gln Lys Leu Phe Ala Asp Ser Trp Met Ala Glu Thr Phe Ala Lys Asp
    240                 245                 250 cca aaa gcc ggc gca agc gtc ttt gat acc ctc gcc cta gcc tat gcc     1161
Pro Lys Ala Gly Ala Ser Val Phe Asp Thr Leu Ala Leu Ala Tyr Ala
255                 260                 265                 270 atc gac cca agt tac gca aca aaa gtg gac gat ctc tat atg gac gtc     1209
Ile Asp Pro Ser Tyr Ala Thr Lys Val Asp Asp Leu Tyr Met Asp Val
                275                 280                 285 gat atc gct ttt ggc cca ggc tat ggc cgc act ctt ggc tat tgg cag     1257
Asp Ile Ala Phe Gly Pro Gly Tyr Gly Arg Thr Leu Gly Tyr Trp Gln
            290                 295                 300 aag cag cca acg cca cta ttg caa aag atg aaa gta gta aaa gag ttc     1305
Lys Gln Pro Thr Pro Leu Leu Gln Lys Met Lys Val Val Lys Glu Phe
        305                 310                 315 gac aaa aag cgc ttc ttt gat ctc tac gtg gat ttg atg cag cgt ccg     1353
Asp Lys Lys Arg Phe Phe Asp Leu Tyr Val Asp Leu Met Gln Arg Pro
    320                 325                 330 gtg cca atc aag ttc gaa aaa taaagataaa ggcggctccg gttaagattg         1404
Val Pro Ile Lys Phe Glu Lys
335                 340
```

```
tatcgctggt atcgccctat ctatttgttt ttacgcatta tccaacaaaa aaaccgcttc    1464
gtacttttgc tggaaatgcc ttattctctt gcctctcggg atttgccggg aggcaaatgc    1524
aatttgtggg gccaggcatt aatggc                                         1550
```

<210> SEQ ID NO 2
<211> LENGTH: 363
<212> TYPE: PRT
<213> ORGANISM: Ochrobactrum anthropi

<400> SEQUENCE: 2

```
Met Lys Arg Ile Leu Ala Ala Val Cys Ile Ala Ala Ser Thr Leu Leu
        -20             -15             -10

Ala Leu Pro Ala Gln Ala Asp Thr Glu Lys Met Ile Ile Asp Thr Asp
 -5              -1   1               5                       10

Phe Ser Thr Ile Gly Asp Asp Gly Gln Val Leu Ile Met Ala Ala Gln
                 15              20                  25

Leu Tyr Lys Gln Gly Ala Ile Asp Leu Leu Gly Val Thr Val Val Thr
            30              35              40

Gly Asn Asn Trp Leu Lys Gln Glu Val Ala Asp Ala Leu Arg Ala Val
        45              50              55

Glu Arg Leu Gly Ile Glu Asp Lys Val Gly Val Tyr Ala Gly Ala Asn
 60              65                  70

Leu Pro Leu Val His Asp Pro Arg Ser Phe Glu Ser Glu Arg Ala Leu
 75              80              85                       90

Phe Gly Phe Gly Glu Ser Tyr Lys Thr Ala Phe His Arg Pro Glu Pro
                 95              100                 105

Thr Glu Lys Asp Leu Ile Ala Pro Pro Asp Gly Phe Ala Lys Lys Ala
            110             115                 120

Lys Leu Glu Lys Glu Asp Ala Val Asp Phe Ile Val Asn Thr Val Lys
        125             130                 135

Ala Asn Pro Asn Glu Val Thr Leu Leu Val Ile Gly Pro Val Thr Asn
 140                 145             150

Val Ala Leu Ala Ile Arg Lys Ser Pro Glu Ile Val Pro Leu Ile Lys
155             160                 165                 170

Arg Ile Val Tyr Met Ala Gly Ala Val Asp Val Lys Gly Asn Thr Thr
                175             180                 185

Pro Ala Ala Glu Met Asn Val Trp Val Asp Pro Glu Ala Ala Arg Ile
            190             195                 200

Val Met Arg Ala Pro Ile Glu Gln Ala Met Ile Pro Leu Asp Val Thr
        205             210             215

Asp Ile Thr Gln Leu Asp Lys Glu Thr Phe Asp Arg Val Ile Ala Gly
 220                 225             230

Asp Gly Pro Val Gln Lys Leu Phe Ala Asp Ser Trp Met Ala Glu Thr
235                 240             245             250

Phe Ala Lys Asp Pro Lys Ala Gly Ala Ser Val Phe Asp Thr Leu Ala
                255                 260             265

Leu Ala Tyr Ala Ile Asp Pro Ser Tyr Ala Thr Lys Val Asp Asp Leu
            270             275             280

Tyr Met Asp Val Asp Ile Ala Phe Gly Pro Gly Tyr Gly Arg Thr Leu
        285             290             295

Gly Tyr Trp Gln Lys Gln Pro Thr Pro Leu Leu Gln Lys Met Lys Val
300             305             310
```

```
Val Lys Glu Phe Asp Lys Lys Arg Phe Phe Asp Leu Tyr Val Asp Leu
315                 320                 325                 330

Met Gln Arg Pro Val Pro Ile Lys Phe Glu Lys
                335                 340

<210> SEQ ID NO 3
<211> LENGTH: 15
<212> TYPE: PRT
<213> ORGANISM: Ochrobactrum anthropi

<400> SEQUENCE: 3

Asp Thr Glu Lys Met Ile Ile Asp Thr Asp Phe Ser Thr Ile Gly
1               5                   10                  15

<210> SEQ ID NO 4
<211> LENGTH: 4
<212> TYPE: PRT
<213> ORGANISM: Ochrobactrum anthropi

<400> SEQUENCE: 4

Glu Phe Asp Lys
1

<210> SEQ ID NO 5
<211> LENGTH: 11
<212> TYPE: PRT
<213> ORGANISM: Ochrobactrum anthropi
<220> FEATURE:
<221> NAME/KEY: MOD_RES
<222> LOCATION: (1)..(11)
<223> OTHER INFORMATION: Xaa at position 10 signifies an undecodable
      residue.

<400> SEQUENCE: 5

Thr Ala Phe His Arg Pro Glu Pro Thr Xaa Lys
1               5                   10

<210> SEQ ID NO 6
<211> LENGTH: 15
<212> TYPE: PRT
<213> ORGANISM: Ochrobactrum anthropi

<400> SEQUENCE: 6

Glu Thr Phe Asp Arg Val Ile Ala Gly Asp Gly Pro Val Gln Lys
1               5                   10                  15

<210> SEQ ID NO 7
<211> LENGTH: 12
<212> TYPE: PRT
<213> ORGANISM: Ochrobactrum anthropi
<220> FEATURE:
<221> NAME/KEY: MOD_RES
<222> LOCATION: (1)..(12)
<223> OTHER INFORMATION: Xaa at position 1 signifies an undecodable
      residue.

<400> SEQUENCE: 7

Xaa Ile Val Tyr Met Ala Gly Ala Val Asp Val Lys
1               5                   10

<210> SEQ ID NO 8
<211> LENGTH: 11
<212> TYPE: PRT
<213> ORGANISM: Ochrobactrum anthropi

<400> SEQUENCE: 8
```

```
Asp Leu Ile Ala Pro Pro Asp Gly Phe Ala Lys
  1               5                  10

<210> SEQ ID NO 9
<211> LENGTH: 12
<212> TYPE: PRT
<213> ORGANISM: Ochrobactrum anthropi

<400> SEQUENCE: 9

Glu Asp Ala Val Asp Phe Ile Val Asn Thr Val Lys
  1               5                  10

<210> SEQ ID NO 10
<211> LENGTH: 32
<212> TYPE: PRT
<213> ORGANISM: Ochrobactrum anthropi
<220> FEATURE:
<221> NAME/KEY: MOD_RES
<222> LOCATION: (1)..(32)
<223> OTHER INFORMATION: Xaa at position 21 signifies an undecodable
      residue.

<400> SEQUENCE: 10

Val Gly Val Tyr Ala Gly Ala Asn Leu Pro Leu Val His Asp Pro Arg
  1               5                  10                  15

Ser Phe Glu Ser Xaa Arg Ala Leu Phe Gly Phe Gly Glu Ser Tyr Lys
                 20                  25                  30

<210> SEQ ID NO 11
<211> LENGTH: 13
<212> TYPE: PRT
<213> ORGANISM: Ochrobactrum anthropi

<400> SEQUENCE: 11

Leu Phe Ala Asp Ser Trp Met Ala Glu Thr Phe Ala Lys
  1               5                  10
```